United States Patent
Scanlon

(10) Patent No.: US 11,103,853 B2
(45) Date of Patent: Aug. 31, 2021

(54) PROCESS FOR RECOVERING VIRAL PRODUCTS USING FUNCTIONALISED CHROMATOGRAPHY MEDIA

(71) Applicant: Puridify Ltd., Hertfordshire (GB)

(72) Inventor: Ian Scanlon, Cambridgeshire (GB)

(73) Assignee: Puridify Ltd., Hertfordshire (GB)

( * ) Notice: Subject to any disclaimer, the term of this patent is extended or adjusted under 35 U.S.C. 154(b) by 0 days.

(21) Appl. No.: 16/314,943

(22) PCT Filed: Jul. 14, 2017

(86) PCT No.: PCT/GB2017/052084
§ 371 (c)(1),
(2) Date: Jan. 3, 2019

(87) PCT Pub. No.: WO2018/011599
PCT Pub. Date: Jan. 18, 2018

(65) Prior Publication Data
US 2019/0255513 A1      Aug. 22, 2019

(30) Foreign Application Priority Data

Jul. 14, 2016  (GB) .................................... 1612248

(51) Int. Cl.
*B01J 20/285* (2006.01)
*A61P 35/00* (2006.01)
(Continued)

(52) U.S. Cl.
CPC ......... *B01J 20/285* (2013.01); *A61K 48/0091* (2013.01); *A61P 35/00* (2018.01);
(Continued)

(58) Field of Classification Search
None
See application file for complete search history.

(56) References Cited

U.S. PATENT DOCUMENTS

| 10,017,746 B2 | 7/2018 | Sheldon et al. | |
| 2005/0042740 A1* | 2/2005 | Qu | C12N 7/00 435/239 |
| 2016/0288089 A1* | 10/2016 | Hardick | B01J 41/07 |

FOREIGN PATENT DOCUMENTS

| JP | 2007-117003 A | 5/2007 |
| JP | 2010-193720 A | 9/2010 |

(Continued)

OTHER PUBLICATIONS

Ma et al. "Electrospun cellulose nanofiber as affinity membrane" Journal of Membrane Science, 265, 2005, p. 115-123 (Year: 2005).*
(Continued)

*Primary Examiner* — Ryan B Huang
(74) *Attorney, Agent, or Firm* — Eversheds Sutherland (US) LLP

(57) ABSTRACT

The present invention provides a process for recovering a viral product from a composition comprising said product and product-related impurities, which process comprises contacting the composition with a functionalised chromatography medium comprising one or more polymer nanofibres, wherein the viral product comprises a plurality of viruses, virus particles/virions, viral cores, membrane-stripped viruses, viral cores with outer membrane(s) removed and/or capsids removed, or proviruses, each of which contains one or more polynucleotides, and wherein the product-related impurities comprise a plurality of viruses, virus particles/virions, virus-like particles, viral cores, membrane-stripped viruses, viral cores with outer membrane(s) removed and/or capsids removed or proviruses, each of which is substantially devoid of polynucleotides.

13 Claims, 10 Drawing Sheets

(51) Int. Cl.
*A61K 48/00* (2006.01)
*B01J 20/28* (2006.01)
*C12N 7/00* (2006.01)
*C12N 7/02* (2006.01)

(52) U.S. Cl.
CPC .......... *B01J 20/28038* (2013.01); *C12N 7/00* (2013.01); *C12N 7/02* (2013.01); *C12N 2710/10051* (2013.01); *C12N 2750/14151* (2013.01); *C12N 2799/022* (2013.01); *C12N 2799/025* (2013.01)

(56) References Cited

FOREIGN PATENT DOCUMENTS

| | | |
|---|---|---|
| WO | 97/08298 A1 | 3/1997 |
| WO | 2004/113494 A2 | 12/2004 |
| WO | 2007/017085 A2 | 2/2007 |
| WO | 2008/095709 A1 | 8/2008 |
| WO | 2011/045381 A1 | 4/2011 |
| WO | 2011/094198 A1 | 8/2011 |
| WO | 2011/154976 A2 | 12/2011 |
| WO | 2012/015908 A2 | 2/2012 |
| WO | 2013/068741 A1 | 5/2013 |
| WO | 2015/052460 A1 | 4/2015 |

OTHER PUBLICATIONS

PCT International Search Report and Written Opinion for PCT Application No. PCT/GB2017/052084 dated Dec. 22, 2017 (18 pages).

GB Search Report for GB Application No. 1612248.3 dated Mar. 24, 2017 (5 pages).

Hardick et al., "Nanofiber adsorbents for high productivity downstream processing," Journal of Biotechnology, 2015, 213:74-82.

Segura et al., "Chromatography Purification of Canine Adenoviral Vectors," Human Gene Therapy, 2012, 23 (3):182-197.

Vellekamp et al., "Empty Capsids in Column-Purified Recombinant Adenovirus Preparations," Human Gene Therapy, 2001, 12(15):1923-1936.

Japanese Office Action for JP Application No. 2019-500819 dated May 10, 2021 (10 pages with English translation).

* cited by examiner

PROCESS FOR RECOVERING VIRAL PRODUCTS USING FUNCTIONALISED CHROMATOGRAPHY MEDIA

CROSS REFERENCE TO RELATED APPLICATIONS

This application claims the priority benefit of PCT/GB2017/052084 filed on Jul. 14, 2017 which claims priority benefit of Great Britain Application No. 1612248.3 filed Jul. 14, 2016. The entire contents of which are hereby incorporated by reference herein.

FIELD OF THE INVENTION

The invention relates to processes for recovering viral products, typically packed viral vectors, from compositions comprising both viral products and product-related impurities, typically unpacked viruses. The process involves contacting the composition with a functionalized chromatography medium comprising one or more polymer nanofibres.

INTRODUCTION

The biotechnology market is the fastest growing sector within the world pharmaceutical market, accounting for 20% ($153bn) of all market sales in 2012. This growth from 10% of the market share in 2002 is set to grow by 41% between 2012 and 2018 from $153bn to $215bn.

One area which represents much potential for future growth is gene therapy. Such methods of therapy have the potential to correct hereditary genetic defects, or manipulate cells either ex vivo or in-vivo to treat diseases such as cancer (Davila et al., 2014), hemophilia (Nathwani et al., 2014) and Parkinson's Disease (Kaplitt et al.).

In methods of gene therapy, delivery of a gene of interest into a cell requires the use of a vector. Many such vectors being developed for clinical application are derived from recombinant viruses such as adenovirus (AdV), adeno-associated virus (AAV) and lentivirus (LV). The purpose of the vector in gene therapy is to deliver a nucleic acid sequence (DNA or RNA) to the cell where it undergoes processing by the cell's biochemical machinery to alter the cell's properties to yield the desired therapeutic effect.

The vector material is typically generated from cell lines that have been modified to produce the constituent parts of the vector e.g. its coat or capsid, and the nucleic acid material that is intended to be delivered to the cells. During the vector production process the nucleic acid sequence needs to be incorporated into the vector to form a "packed" or "full" vector. "Active" or "Infective" vectors are "packed" vectors that can successfully infect the target cell resulting in the expression the nucleic acid sequence. "Empty" or "unpacked" vectors essentially devoid of nucleic acid material are also produced in typical vector production processes. Thus, during the production of the vectors a mixed population is generated containing a mixture of the aforementioned variants.

The separation of Packed vectors from Empty vectors has typically been performed at lab scale through the use of density gradient centrifugation, for instance CsCl (Vellekamp et al., 2001) or iodixanol gradients (Martin Lock et al., 2010) which utilize density differences for the separation. However for industrial scale purification to treat large patient populations such methods are unsuitable, since they pose practical challenges in scaling-up. Therefore certain chromatographic separation methods have been applied as they are inherently more scalable.

For the separation of full AAV vectors from empty vectors a number of commercially available porous bead-based system have been used in ion exchange separations (Urabe et al., 2006), (Qu et al., 2007). Similar separation has also been reported using monoliths with anion exchange functionality (M. Lock, Alvira, & Wilson, 2012). Furthermore (Lee, Kim, & Seol, 2009) reported that infectious AdV material could be separated from defective AdV particles using a metal affinity membrane.

However there are drawbacks in using these known adsorbent materials for chromatographic separations, including separations of packed viral vectors from unpacked vectors. Thus, whilst conventional porous beads have a high capacity, it is not possible to operate packed bed systems comprising such beads at high flowrates.

That is because in a porous bead-based system, the binding event between target molecule/impurity and the solid phase is dependent on diffusion into the porous bead, meaning binding capacity drops off with decreasing residence times. High flowrates are also particularly incompatible with porous beads at manufacturing scale where many litres of bead suspension are packed into a column. Here the mechanical instability of the porous beads can lead to compression or collapse events, which in turn results in a non-homogeneous column bed.

Typical binding capacities for porous beads are in the region of 35-120 mg/mL dependant on the functionality of the solid phase and species bound. However, the low typical flowrates through such systems mean that overall productivities for single column porous bead systems of only around 10-120 mg/mL/min can be achieved.

A further drawback of using porous beads is that the capacity of the material is dependent on the target's ability to access the inner surface area of the bead. Typical porous beads have pore sizes of between 15-30 nm and so have limitations in vector purification where the target vector can be much larger than the pore sizes, examples being AAV (~20 nm), AdV (~80 nm), and LV (~100 nm).

Separations involving membranes and monoliths can be run at far higher flowrates than porous bead-based systems, typical residence times being in the order of 0.2-0.5 minutes. However, typical binding capacities at 10% breakthrough of target for monoliths (10-20 mg/mL) and membranes (7.5-29 mg/mL) under dynamic flow are lower than porous beads (Gottschalk, U. 2008 Biotechnol Prog, 24(3), 496-503. doi: 10.1021/bp070452g). The inferior binding capacity of monolith and membrane materials (compared to porous bead-based materials) can be offset to some extent by utilising higher flowrates. The typical binding capacities and residence times for monoliths and membranes discussed above result in overall productivities of the binding event for monolith and membrane systems around 10-145 mg/mL/min.

Additionally although the pore sizes of membranes are far larger then porous beads, being in the range of 0.2-2 μm the binding capacity of the membranes decreases as the size of the adsorbed species increases (Wickramasinghe, Carlson, Teske, Hubbuch, & Ulbricht, 2006). This emphasizes the need to have both highly porous adsorbents with a high accessible surface area.

There exists a need for chromatography materials that can separate packed from unpacked vectors to enable a therapeutic product to be recovered at industrial scale. The chromatography materials should also share the high binding capacity associated with porous bead-based materials and the higher flowrates that are achievable with monolith/membrane materials. The chromatography materials must also be sufficiently porous so the binding area is accessible to the large vectors and so that suitably high flowrates may be achieved. Such a material would offer high capacity at high flowrates to achieve maximum productivity (product purified/mL/min).

The inventors have surprisingly found that polymer fibre materials, especially polymer nanofibre materials, can be used to separate packed from unpacked vector material. Thus, they have found that such materials have high capacities for vector material at very short residence times, i.e. at high flowrates. This means the materials have advantageously high productivities compared to other adsorbents e.g. beads, membranes, and monoliths. The inventors have also optimized the degrees of polymer grafting and subsequent functionalisation of the polymer fibre materials to improve the resolution of the packed and unpacked species. It has also surprisingly been found that using materials in accordance with the present invention, both packed and unpacked fractions may be eluted at very low salt concentrations (elution conductivities <6 mS). This contrasts with examples in the literature where fractions are not eluted until the conductivity reaches ~12.5 mS (Urabe et al., 2006).

SUMMARY OF THE INVENTION

Accordingly, the present invention provides a process for recovering a viral product from a composition comprising said product and product-related impurities, which process comprises contacting the composition with a functionalised chromatography medium comprising one or more polymer nanofibres,
wherein the viral product comprises a plurality of viruses, virus particles/virions, viral cores, membrane-stripped viruses, viral cores with outer membrane(s) removed and/or capsids removed, or proviruses, each of which contains one or more polynucleotides, and
wherein the product-related impurities comprise a plurality of viruses, virus particles/virions, virus-like particles, viral cores, membrane-stripped viruses, viral cores with outer membrane(s) removed and/or capsids removed or proviruses, each of which is substantially devoid of polynucleotides.

The present invention also provides:
A process for recovering a viral product as defined herein from a composition as defined herein, comprising said product and product-related impurities as defined herein, which process comprises contacting the composition with a salt intolerant chromatography medium, wherein the salt intolerant chromatography medium is capable of eluting the viral product at a conductivity of less than 10 mS/cm.
A process for recovering a viral product as defined herein from a composition as defined herein, comprising said product and product-related impurities as defined herein, which process comprises contacting the composition with a chromatography medium in the form of a membrane or sheet and the composition is passed through a holder comprising one or more said membranes or sheets and optionally one or more frits or other spacer materials,
wherein the composition is passed through the holder such that (a) the path length through said one or more membranes or sheets is less than 2 mm or (b) the total path length through membranes, sheets, frits and other spacer materials is less than 50 mm.
A process for recovering a viral product as defined herein from a composition as defined herein, comprising said product and product-related impurities as defined herein, which process comprises contacting the composition with a chromatography medium in the form of a membrane or sheet and the composition is passed through a holder comprising one or more said membranes or sheets and optionally one or more frits or other spacer materials,
wherein the composition is contacted with the chromatography medium for a period of time of one minute or less.
A process for recovering a viral product from a composition comprising said product and non-product-related impurities, which process comprises contacting the composition with a functionalised chromatography medium comprising one or more polymer nanofibres,
wherein the viral product comprises a plurality of viruses, virus particles/virions, viral cores, membrane-stripped viruses, viral cores with outer membrane(s) removed and/or capsids removed, or proviruses, each of which contains one or more polynucleotides, and
wherein the non-product-related impurities comprise cells and/or cell components such as lipids, host cell proteins and/or other constituent parts of the host cell growth media such as proteins and/or sugars.
A process for recovering a viral product from a composition comprising said product, product-related impurities and non-product-related impurities, as defined herein, which process comprises contacting the composition with a functionalised chromatography medium as defined herein.
A viral product obtainable or obtained by the process of the present invention.
A product-related impurity obtainable or obtained by the process of the present invention.
A composition comprising a viral product of the invention in association with a pharmaceutically acceptable carrier or diluent.
A composition comprising a product-related impurity of the invention in association with a pharmaceutically acceptable carrier or diluent.
A method of microbial treatment, vaccination or gene therapy, which method comprises administering to a patient in need of such therapy an effective amount of a viral product of the invention or a composition of the invention.
A viral product of the invention or a composition of the invention for use in a method of microbial treatment, vaccination or gene therapy.
An ex-vivo method of inserting a polynucleotide into a cell, which method comprises contacting the cell with a viral product of the invention.
A cell obtained or obtainable by the ex-vivo method of the invention.
A method of treatment which comprises administering to a patient in need thereof one or more cells of the invention.
A cell of the invention, for use in a method of treating the human or animal body by therapy.
A cell of the invention, for use in treating cancer.

DETAILED DESCRIPTION OF THE INVENTION

Figure 1:
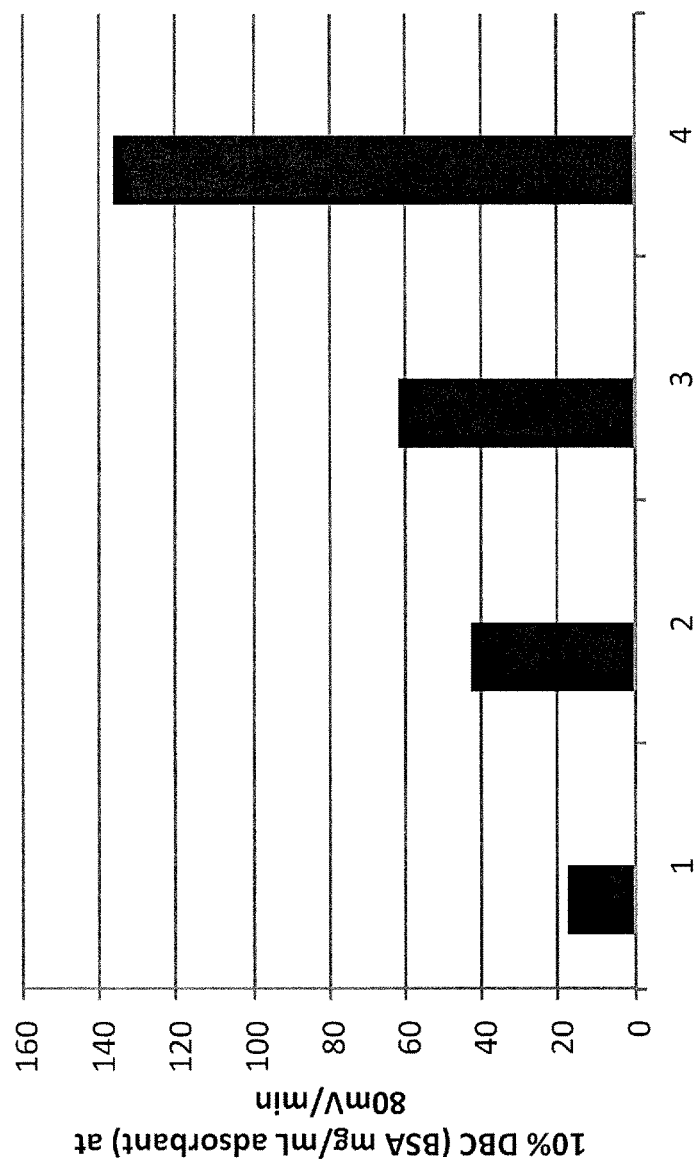
FIG. 1 shows the DBC for BSA for a number of different functionalised chromatography materials.

The present invention is a process for recovering a viral product from a composition comprising said product and product-related impurities, which process comprises contacting the composition with a functionalized chromatography medium comprising one or more polymer nanofibres.

In another embodiment, the present invention is a process for recovering a viral product from a composition comprising said product and non-product-related impurities, which process comprises contacting the composition with a functionalized chromatography medium comprising one or more polymer nanofibres.

Viral Product

The viral product typically comprises a plurality of viruses, virus particles/virions, viral cores, membrane-stripped viruses, viral cores with outer membrane(s) removed and/or capsids removed, or proviruses, each of which contains one or more polynucleotides. Thus, typically, the viral product is a "packed" or "full" viral product, i.e. a "packed" or "full" virus, virus particle/virion, viral core, membrane-stripped virus, viral core with outer membrane(s) removed and/or capsid removed, or provirus. The skilled person is well aware of the concept of "packed" or "full" viruses and related viral products.

Typically, the viral product comprises a plurality of viruses, virus particles, viral cores, membrane-stripped viruses, viral cores with outer membrane(s) removed and/or capsids removed, or proviruses, each of which is capable of infecting a cell. Thus, typically, the viral product is an "active" or "infective" viral product that can successfully infect a target cell. The skilled person is well aware of the concept of "active" or "infective" viruses and related viral products.

Typically, the viral product comprises a plurality of viral vectors each containing one or more transgenic polynucleotides. Thus, the process of the present invention typically a process for recovering one or more viral vectors from a composition comprising said viral vectors and product-related impurities, as defined herein.

The one or more viral vectors each typically contain one or more transgenic polynucleotides or transgenes. It will be understood that the term "transgenic polynucleotide" or "transgene" is used herein to denote a polynucleotide that is not native to a virus.

Preferably, the viral product comprises one or more viruses. In principle any virus may be used. For viral vectors for use in gene therapy the virus is typically a recombinant genetically engineered virus. The recombinant virus typically contains a transgene. Such a transgene could for example encode a biologically functional protein or peptide, an antisense molecule, or a marker molecule. For viral vectors for use in 'virotherapy' the virus may be a wild type lytic virus or a genetically modified version, including conditionally replicating forms that have been 'armed' with transgenes designed to modify virus activity (e.g. transgenes encoding proteins intended to enhance virus spread through solid tumours) or to improve anticancer activity (e.g. transgenes encoding an immune stimulating protein or GDEPT protein), and also including viruses engineered to encode other viruses and produce them upon infection. For viral vectors for use in viral vaccination the virus is often genetically modified adenovirus (including non human adenovirus), herpes virus or vaccinia encoding transgenes as antigens.

In all cases, the virus is either an RNA or DNA virus and is optionally from one of the following families and groups: Adenoviridae; Alfamoviruses; Bromoviridae; Alphacryptoviruses; Partitiviridae: Baculoviridae; Badnaviruses; Betacryptoviruses; Partitiviridae; Bigeminiviruses; Geminiviridae; Birnaviridae; Bromoviruses; Bromoviridae; Bymoviruses; Potyviridae; Bunyaviridae; Caliciviridae; Capillovirus group; Carlavirus group; Carmovirus group; Caulimovirus group; Closterovirus group; *Commelina* yellow mottle virus group; Comovirus virus group; Coronaviridae; PM2 phage group; Corcicoviridae; Cryptic virus group; Cryptovirus group; Cucumovirus virus Φ6 phage group; Cystoviridae; Cytorhabdoviruses; Rhabdoviridae; Carnation ringspot group; Dianthovirus virus group; Broad bean wilt group; Enamoviruses; Fabavirus virus group; Fijiviruses; Reoviridae; Filoviridae; Flaviviridae; Furovirus group; Geminivirus group; Giardiavirus group; Hepadnaviridae; Herpesviridae; Hordeivirus virus group; Hybrigeminiviruses; Geminiviridae; Idaeoviruses; Ilarvirus virus group; Inoviridae; Ipomoviruses; Iriodoviridae; Leviviridae; Lipothrixviridae; Luteovirus group; Machlomoviruses; Macluraviruses; Marafivirus virus group; Maize chlorotic dwarf virus group; Icroviridae; Monogeminiviruses: Geminiviridae; Myoviridae; Nanaviruses; Necrovirus group; Nepovirus virus group; Nodaviridae; Nucleorhabdoviruses: Rhabdoviridae; Orthomyxoviridae; Oryzaviruses: Reoviridae; Ourmiaviruses; Papovaviridae; Paramyxoviridae; Parsnip yellow fleck virus group; Partitiviridae; Parvoviridae including adeno-associated viruses; Pea enation mosaic virus group; Phycodnaviridae; Phytoreoviruses: Reoviridae; Picornaviridae; Plasmarviridae; Podoviridae; Polydnaviridae; Potexvirus group; Potyvirus; Poxviridae; Reoviridae; Retroviridae; Rhabdoviridae; Rhizidiovirus group; Rymoviruses: Potyviridae; Satellite RNAs; Satelliviruses; Sequiviruses: Sequiviridae; Sobemoviruses; Siphoviridae; Sobemovirus group; SSVI-Type Phages; Tectiriviridae; Tenuivirus; Tetravirirdae; Tobamovirus group; Tobravirus group; Togaviridae; Tombusvirus group; Tospoviruses: Bunyaviridae; Torovirus group; Totiviridae; Tymoviruses; Tymovirus group; Plant virus satellites; Umbraviruses; Unassigned potyviruses: Potyviridae: Unassigned rhabdoviruses: Rhabdoviridae; Varicosaviruses; Waikaviruses: Sequiviridae; Ungrouped viruses.

Preferably, the virus is chosen from the Adenoviridae, Parvoviridae including adeno-associated viruses and Retroviridae families.

A particularly preferred virus for use in the invention is an adenovirus, adenoassociated virus, or lentivirus. Adenovirus and adenoassociated are especially preferred, and adenoassociated virus is more preferred.

In some embodiments, a component of a virus may be used, for example a viral core or a provirus (from e.g. pox viruses). However, it is preferred to use a virus or virus particle/virion.

The skilled person is well aware of the meaning of the term "polynucleotide". Such polynucleotides include synthetic molecules such as siRNA molecules, as well as DNA or RNA.

For the avoidance of doubt, a "polynucleotide" is a polynucleoside formed from a plurality of linked individual nucleoside units coupled to each other by any of the numerous known internucleoside linkages. Such internucleoside linkages include, without limitation, the natural internucleoside phosphodiester bond or indeed modified internucleosides such as, but not limited to, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "polynucleotide" also encompasses polynucleosides having one or more stereospecific internucleoside linkages (e. g., (Rp)- or (Sp)-phosphorothioate, alkylphosphonate, or phosphotriester linkages). As used herein, the term "polynucleotide" is expressly intended to include polynucleosides having any such internucleoside linkage, whether or not the linkage comprises a phosphate group. In certain preferred embodiments, these internucleoside linkages may be phosphodiester, phosphorothioate, or phosphorodithioate linkages, or combinations thereof.

The term "polynucleotide" also encompasses polynucleosides having additional substituents including, without limitation, protein groups, lipophilic groups, intercalating agents, diamines, folic acid, cholesterol and adamantane. The term "polynucleotide" also encompasses any other nucleobase containing polymer, including, without limitation, peptide nucleic acids (PNA), peptide nucleic acids with phosphate groups (PHONA), locked nucleic acids (LNA), morpholino-backbone oligonucleotides, and oligonucleotides having backbone sections with alkyl linkers or amino linkers. The alkyl linker may be branched or unbranched, substituted or unsubstituted, and chirally pure or a racemic mixture.

The polynucleotide can include naturally occurring nucleosides, modified nucleosides, or mixtures thereof. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside, as herein described. In some embodiments, the modified nucleoside is a 2'-substituted ribonucleoside, an arabinonucleoside or a 2'-deoxy-2'-substituted-arabinoside.

As used herein, the term "a hybrid polynucleotide" is a polynucleotide having more than one type of nucleoside.

Herein, the term "polynucleotide" includes hybrid and chimeric polynucleotides. A "chimeric polynucleotide" is a polynucleotide having more than one type of internucleoside linkage within its sequence structure. One preferred example of such a chimeric polynucleotide is a chimeric oligonucleotide comprising a phosphorothioate, phosphodiester or phosphorodithioate region and non-ionic linkages such as alkylphosphonate or alkylphosphonothioate linkages (U.S. Pat. Nos. 5,635,377 and 5,366,878).

Herein, the term "polynucleotide" also includes circularized variants and circular polynucleotides.

Preferably, the polynucleotide comprises at least one naturally occurring phosphodiester, or one modified phosphorothioate, or phosphorodithioate internucleoside linkage, however preferred linkages or indeed backbone modifications including, without limitation, methylphosphonates, methylphosphonothioates, phosphotriesters, phosphothiotriesters, phosphorothioates, phosphorodithioates, triester prodrugs, sulfones, sulfonamides, sulfamates, formacetal, N-methylhydroxylamine, carbonate, carbamate, morpholino, boranophosphonate, phosphoramidates, especially primary amino-phosphoramidates, N3 phosphoramidates and N5 phosphoramidates, and stereospecific linkages (e. g., (Rp)- or (Sp)-phosphorothioate, alkylphosphonate, or phosphotriester linkages) are also envisaged.

The sugar moiety of the nucleoside can be a non-naturally occurring sugar moiety. Herein, a "naturally occurring sugar moiety" is a sugar moiety that occurs naturally as part of a nucleic acid, e. g., ribose and 2'-deoxyribose, and a "non-naturally occurring sugar moiety" is any sugar that does not occur naturally as part of a nucleic acid, but which can be used in the backbone for a polynucleotide, for example but not limited to hexose. Arabinose and arabinose derivatives are examples of preferred sugar moieties.

Modified or substituted polynucleotides are often preferred over native forms because of desirable properties such as, for example, enhanced cellular uptake, enhanced affinity for nucleic acid target and increased stability in the presence of nucleases.

As used herein, "polynucleotide" refers both to "oligonucleotides" (a polynucleotide molecule of 18-25 nucleotides in length) and polynucleotides of 26 or more nucleotides. In general, polynucleotides of 26 or more nucleotides may have 100 or more, 500 or more or even 1000 or more nucleotides. In general, polynucleotides typically have fewer than 10,000 nucleotides, for instance fewer than 5,000 nucleotides. Polynucleotides having from 1000 to 10,000 nucleotides may be preferable.

In the case where the virus is adeno-associated virus (AAV), the polynucleotide typically has up to 5000 nucleotides.

In the case where the virus is adenovirus (AV), the polynucleotide typically has up to 8000 nucleotides.

In the case where the virus is lentivirus, the polynucleotide typically has up to 10,000 nucleotides.

Product-Related Impurities

The product-related impurities typically comprise a plurality of viruses, virus particles/virions, virus-like particles, viral cores, membrane-stripped viruses, viral cores with outer membrane(s) removed and/or capsids removed or proviruses, each of which is substantially devoid of polynucleotides. Thus, typically, the product-related impurities are "unpacked" or "empty" viral products, i.e. "unpacked" or "empty" viruses, virus particles/virions, viral cores, membrane-stripped viruses, viral cores with outer membrane(s) removed and/or capsid removed, or proviruses. The skilled person is well aware of the concept of "unpacked" or "empty" viruses and related products.

The product-related impurities may additionally comprise the polynucleotides, not contained within viruses, virus particles/virions, virus-like particles, viral cores, membrane-stripped viruses, viral cores with outer membrane(s) removed and/or capsids removed or proviruses, but rather in free form.

Typically, the product-related impurities comprise a plurality of viruses, virus particles/virions, virus-like particles, viral cores, membrane-stripped viruses, viral cores with outer membrane(s) removed and/or capsids removed or proviruses, each of which is incapable of infecting a cell. Thus, typically, the product-related impurities are "inactive" or "non-infective" products incapable of infecting a cell. The skilled person is well aware of the concept of "inactive" or "non-infective" viruses and related viral products. In some embodiments, the product-related impurities comprise a plurality of viruses, virus particles/virions, virus-like particles, viral cores, membrane-stripped viruses, viral cores with outer membrane(s) removed and/or capsids removed or proviruses, which may or may not comprise polynucleotides, but which are in any case incapable of infecting cells. In such embodiments, the polynucleotide material may, for instance, be incompletely packed within the virus or viral product, meaning the product is incapable of infecting a cell. Typically, the product-related impurities comprise a plurality of viruses, virus particles/virions, virus-like particles viral cores, membrane-stripped viruses, viral cores with outer membrane(s) removed and/or capsids removed or proviruses, each of which lacks a complete viral genome.

Typically, the product-related impurities comprises one or more of the specific viruses or viral components defined above, provided those viruses or viral components have one or more of the characteristics of the product-related impurities also mentioned above, i.e.
- are substantially devoid of polynucleotides;
- are unpacked;
- are empty;
- are incapable of infecting a cell;
- are inactive;
- are non-infective; and/or
- lack a complete viral genome;
- optionally in addition to free polynucleotides.

Thus, preferably, the product-related impurities comprise a plurality of adenoviruses, adenoassociated viruses, or lentiviruses, provided those have one or more of the characteristics of the product-related impurities mentioned above. Adenovirus and adenoassociated are especially preferred, and adenoassociated virus is more preferred.

Non-Product-Related Impurities

The non-product-related impurities typically comprise cells, or cell components such as lipids, host cell proteins and/or other constituent parts of the host cell growth media such as proteins, sugars and so forth.

Thus, typically, the non-product-related impurities comprise cells. Alternatively, the non-product-related impurities comprise cell components such as lipids, host cell proteins, and/or other constituent parts of the host cell growth media such as proteins and/or sugars.

For the avoidance of doubt, the non-product-related impurities are well known to a person skilled in the art.

Polymer Fibres

The functionalised chromatography medium comprises one or more polymer nanofibres, and is typically formed of said one or more polymer nanofibres. Where "nanofibres" are referred to herein, these should be understood to be the polymer nanofibres defined below.

Typically, the polymer nanofibres are in the form of one or more non-woven sheets, each sheet comprising one or more said polymer nanofibres. A non-woven sheet comprising one or more polymer nanofibres is a mat of said one or more polymer nanofibres with each fibre oriented essentially randomly, i.e. it has not been fabricated so that the fibre or fibres adopts a particular pattern. Non-woven sheets comprising polymer nanofibres are typically provided by known methods. Non-woven sheets may, in certain circumstances, consist of a single polymer nanofibre. Alternatively, non-woven sheets may comprise two or more polymer nanofibres, for example 2, 3, 4, 5, 6, 7, 8, 9 or 10 polymer nanofibres.

The polymer nanofibres may be electrospun polymer nanofibres. Such electrospun polymer nanofibres are well known to the person skilled in the art. Alternative methods for producing polymer nanofibres may also be used, e.g. drawing.

Polymer nanofibres for use in the present invention typically have mean diameters from 10 nm to 1000 nm. For some applications, polymer nanofibres having mean diameters from 200 nm to 800 nm are appropriate. Polymer nanofibres having mean diameters from 200 nm to 400 nm may be appropriate for certain applications.

The length of polymer nanofibres for use in the present invention is not particularly limited. Thus, conventional processes e.g. electrospinning can produce polymer nanofibres many hundreds of metres or even kilometres in length. Typically, though, the one or more polymer nanofibres have a length up to 10 km, preferably from 10 m to 10 km.

Non-woven sheets typically have area densities from 1 to 40 $g/m^2$, preferably from 5 to 25 $g/m^2$, in some circumstances from 1 to 20 or 5 to 15 $g/m^2$.

Non-woven sheets typically have a thickness from 5 to 120 µm, preferably from 10 to 100 µm, in some circumstances from 50 to 90 µm, in other circumstances from 5 to 40, 10 to 30 or 15 to 25 µm.

The polymer used to produce the nanofibres used in the processes of the present invention is not particularly limited, provided the polymer is suitable for use in chromatography applications. Thus, typically, the polymer is a polymer suitable for use as a chromatography medium, i.e. an adsorbent, in a chromatography method. Suitable polymers include polyamides such as nylon, polyacrylic acid, polymethacrylic acid, polyacrylonitrile, polystyrene, polysulfones e.g. polyethersulfone (PES), polycaprolactone, collagen, chitosan, polyethylene oxide, agarose, agarose acetate, cellulose, cellulose acetate, and combinations thereof. Polyethersulfone (PES), cellulose and cellulose acetate are preferred. In some cases, cellulose and cellulose acetate are preferred.

In some embodiments, the functionalised chromatography medium comprises one or more nanofibres formed from different polymers. Thus, in this embodiment, the functionalised chromatography medium comprises one or more different polymers. Typical polymers are as defined above.

Typically, the functionalised chromatography medium is a functionalised cellulose chromatography medium. Preferably, the functionalised chromatography medium is formed of one or more non-woven sheets, each comprising one or more cellulose or cellulose acetate nanofibres. Cellulose acetate is readily formed into nanofibres, e.g. by electrospinning and can readily be transformed into cellulose after electrospinning.

Although in a particularly preferred embodiment, the functionalised chromatography medium comprises one or more polymer nanofibres, in an alternative embodiment, the functionalised chromatography medium may comprise one or more of any type of polymer fibre. Such polymer fibres may have any or all of the same properties as the nanofibres described above. Typically, such polymer fibres may have mean diameters from 10 nm to 1000 µm, preferably from 10 nm to 750 µm, more preferably from 10 nm to 500 µm, even more preferably from 10 nm to 400 µm, even more preferably from 10 nm to 300 µm, even more preferably from 10 nm to 200 µm, even more preferably from 10 nm to 100 µm, even more preferably from 10 nm to 75 µm, even more preferably from 10 nm to 50 µm, even more preferably from 10 nm to 40 µm, even more preferably from 10 nm to 30 µm, even more preferably from 10 nm to 20 µm, even more preferably from 10 nm to 10 µm, even more preferably from 10 nm to 5 µm, even more preferably from 10 nm to 4 µm, even more preferably from 10 nm to 3 µm, even more preferably from 10 nm to 2 µm, even more preferably from 10 nm to 1 µm (1000 nm).

Functionalised Chromatography Medium

As discussed above, the functionalized chromatography medium with which the composition is contacted comprises one or more polymer nanofibres. The polymer nanofibres optionally have one or more polymer chains, which may be the same or different, covalently bonded thereto. However, in certain preferred embodiments, the nanofibres have no polymer chains covalently bonded thereto. The nanofibres are typically functionalised, typically with one or more ligand groups, which may be the same or different, and which render the nanofibres comprising the one or more ligand groups suitable for use as a chromatography medium.

Prior to bonding a polymer to the nanofibres, or functionalizing with one or more ligand groups, the one or more polymer nanofibres, which may be in the form or one or more non-woven sheets, may optionally be physically modified by heating and/or pressing the polymer nanofibres/non-woven sheets, preferably heating and pressing the polymer nanofibres/non-woven sheets. These steps improve the structural stability of the material. The pressing and heating conditions may also be varied to alter the thickness and/or porosity of the resultant material.

Use of multiple non-woven sheets of polymer nanofibres enables a thicker material to be prepared which has a greater capacity for adsorbence. The functionalised chromatography medium is typically therefore formed by providing two or more non-woven sheets stacked one on top of the other, each said sheet comprising one or more polymer nanofibres, and simultaneously heating and pressing the stack of sheets to fuse points of contact between the nanofibres of adjacent sheets.

In the case of a cellulose functionalised chromatography medium, this is typically formed by providing two or more non-woven sheets stacked one on top of the other, each said sheet comprising one or more cellulose acetate nanofibres, and simultaneously heating and pressing the stack of sheets to fuse points of contact between the nanofibres of adjacent sheets.

Preferred processing conditions for pressing and heating of polymer nanofibres/non-woven sheets can be found in WO-A-2015/052460 and WO-A-2015/052465, the entirety of which are incorporated herein by reference.

As mentioned above, the polymer nanofibres, which may be in the form or one or more non-woven sheets and which may optionally have been physically modified by heating and/or pressing, optionally have one or more polymer chains, which may be the same or different, covalently bonded thereto. In certain embodiments, said polymer nanofibres do not have polymer chains bonded thereto, in particular when the virus is adenoassociated virus (AAV).

Covalently bonding one or more polymer chains to the polymer nanofibres may involve either grafting a preformed polymer chain to the nanofibres, or grafting a polymer chain from the nanofibres.

For the avoidance of doubt, the polymer chains are not the same as the nanofibres. Thus, a typical fabrication process would involve providing one or more said polymer nanofibres, optionally in the form of one or more said non-woven sheets, and grafting one or more preformed polymer chains to the nanofibres/sheets and/or grafting one or more polymer chains from the nanofibres/sheets. Grafting one or more chains from the nanofibres/sheets is preferred.

Grafting a preformed polymer chain to the nanofibres typically involves reacting a preformed polymer chain having at least one group capable of reacting with a functional group on the nanofibres.

Grafting one or more polymer chains from the substrate typically comprises growing one or more polymer chains from one or more functional groups present on the nanofibres, optionally in the presence of one or more catalysts.

Thus, typically, the nanofibres comprise one or more functional groups, preferably one or more functional groups to which a preformed polymer chain may be grafted and/or from which a polymer chain may be grown.

Growing a polymer chain from the one or more functional groups means building up a polymer at the one or more functional groups from individual monomer building blocks.

The polymer chains may be neutral or charged. In certain embodiments, neutral polymer chains are preferred.

Neutrality of a polymer can be assessed by whether the polymer contains any groups which would be ionisable, i.e. protonated or deprotonated, at essentially neutral pH, e.g. pH 6-8, typically pH 6.5-7.5, usually pH 6.75-7.25, or about pH 7. Typically, a neutral polymer contains substantially no acidic or basic centres, i.e. substantially no functional groups that are protonated or deprotonated at pH 6-8, typically pH 6.5-7.5, usually pH 6.75-7.25, or about pH 7. This can be determined by a skilled person by assays typical in the art. Typical procedures for the assessment of acidity and basicity, along with the theoretical aspects thereof are discussed in "Acidity and basicity of solids: Theory, assessment and utility" Editors J. Fraisard and L. Petrakis, NATO ASI Series C, volume 444, Kluwer Academic Publishers, Dordrecht, Boston and London, 1994, especially pp. 513, the entirety of which is incorporated herein by reference. As used here, substantially means fewer than 1 mol %, preferably fewer than 0.1 mol %, even more preferably fewer than 0.01 mol %, or even fewer than 0.001 mol %.

Typically, only one type of polymer is covalently bonded to the nanofibres. However, in other embodiments, more than one type of polymer may be covalently bonded to the nanofibres.

In embodiments where the functionalised chromatography medium is formed from more than one kind of polymer nanofibre, i.e. nanofibres formed from more than one kind of polymer, each different kind of polymer nanofibre may be covalently bonded to a polymer chain formed from a different kind of polymer. That could, for instance, result from different functional groups being present on the different polymer nanofibres. Alternatively, the same polymer may be covalently bonded to each of the different kinds of polymer nanofibres.

Typical functional groups include hydroxyl, amino and carboxyl groups. In the case where the functionalised chromatography medium is formed of one or more cellulose or cellulose acetate nanofibres, the functional groups are typically hydroxyl groups.

Typically, the nanofibres are treated to introduce the one or more functional groups, or the nanofibres are treated to deprotect or activate any functional groups, or the nanofibres are treated to increase the number/density of functional groups. Preferably, the nanofibres are treated to deprotect any functional groups on the substrate.

Deprotection of the functional groups is typically effected so that the functional groups can have one or more polymer chains grown from them or one or more preformed polymer chains grafted to them. Deprotection may also be carried out so that the nanofibres may be functionalised with one or more ligand groups as discussed further below.

For instance, when the chromatography medium is a cellulose chromatography medium, typically cellulose acetate nanofibres are provided and, prior to covalently bonding any polymer thereto or functionalizing with one or more ligand groups, the cellulose acetate is treated to convert it to cellulose. This involves the deprotection of acetylated hydroxyl groups to give hydroxyl groups. Conversion of cellulose acetate to cellulose is typically effected using aqueous alkali, preferably NaOH in water: ethanol, more preferably water:ethanol 2:1, for a period of greater than 12 hrs, for example from 12 to 36 hours. The same protocol may also be used when deprotecting acetylated hydroxyl groups prior to functionalising with one or more ligand groups.

Activation of functional groups is discussed further below in the context of functionalising with one or more ligand groups. That discussion applies equally to activation of functional groups prior to covalently bonding one or more polymer chains to the nanofibres.

Methods for increasing the number/density of functional groups on the substrate will be known to the skilled person.

When the one or more functional groups are introduced to the nanofibres, one or more functional groups present on the nanofibres are modified to introduce a functional group (a) to which a preformed polymer chain may be grafted and/or (b) from which one or more polymer chains may be grown. The introduction step may involve a single step or multiple steps that together modify the functional group present on the nanofibres to a functional group to/from which one or more polymer chains may be grafted.

The one or more polymer chains may be branched, resulting in a "bush" type structure. Alternatively, essentially unbranched polymer chains may be used, resulting in a "brush" polymer structure. In certain embodiments, unbranched polymer chains are preferred.

Functionalisation

The processes of the present invention utilize functionalised chromatography media. The chromatography medium is typically functionalised with one or more ligand groups, which render the material suitable for use as a chromatography medium. The ligand groups are typically carried on the polymer nanofibres. Thus, typically the one or more polymer nanofibres are functionalised with one or more ligand groups, which may be the same or different, and which render the nanofibres comprising the one or more ligand groups suitable for use as a chromatography medium.

The polymers used to form the nanofibres may be functionalised prior to the step of forming the nanofibres.

Alternatively, and preferably, the nanofibres are functionalised after the polymer has been formed into nanofibres.

Typically, the one or more ligand groups are bonded to the one or more nanofibres. This is typical in the case where the nanofibres do not have one or more polymer chains covalently bonded thereto. Thus, typically, the nanofibres do not have one or more polymer chains covalently bonded thereto and the one or more ligand groups are bonded to the one or more nanofibres.

Alternatively, when the nanofibres have one or more polymer chains covalently bonded thereto, the one or more ligand groups may be covalently bonded to the nanofibres and/or the polymer chains. In this case, the one or more ligand groups are preferably covalently bonded to at least the one or more polymer chains.

The one or more ligand groups may typically be introduced by contacting the one or more nanofibres, which have been optionally pressed and/or heated and which optionally have one or more polymer chains covalently bonded thereto, with a reagent, which functionalises the product as a chromatography medium.

The reagent typically functionalises the chromatography medium by introducing one or more ligand groups which render the functionalised product comprising the one or more ligand groups suitable for use as a chromatography medium. The ligand groups are the groups introduced onto the grafted product that make it suitable for use as a chromatography medium. Suitable ligand groups and reagents are discussed further below.

In some embodiments, the functionalised chromatography medium is functionalised with only one type of ligand group. In other embodiments, the functionalised chromatography medium is functionalised with two or more types of ligand group.

In embodiments where the functionalised chromatography medium comprises one or more polymer nanofibres formed from different polymers, each different kind of polymer nanofibre may be functionalised (after optional covalent bonding of polymer chains thereto) with one or more ligand groups, which may be the same or different.

In embodiments where more than one type of polymer chain may be covalently bonded to the nanofibres, each polymer chain may be functionalised with one or more ligand groups, which may be the same or different.

In general terms, the functionalisation of the medium/nanofibres changes their chemical and/or physical properties. This in turn affects how the functionalised chromatography medium behaves when used in a chromatography method. The modifications may, for example, change the polarity, hydrophobicity or biological binding properties of the functionalised chromatography medium compared to its unfunctionalised form. The modifications may, in certain circumstances, change more than one of the polarity, hydrophobicity or biological binding properties of the functionalised chromatography medium compared to its unfunctionalised form. In one embodiment, the modification changes the polarity and hydrophobicity of the functionalised chromatography medium compared to its unfunctionalised form.

Typically, the functionalised chromatography media are suitable for use in chromatography methods chosen from ion exchange chromatography, affinity capture chromatography, hydrophobic chromatography and mixed mode chromatography. In certain circumstances, the chromatography method operates in "mixed mode", i.e. utilising more than one form of interaction, i.e. ion exchange, affinity capture and hydrophobic interaction. Typically, such "mixed mode" chromatography involves ion exchange (ionic) and hydrophobic interactions. Preferably, the functionalised chromatography media are suitable for use in chromatography methods chosen from ion exchange chromatography, affinity capture chromatography, and hydrophobic chromatography, preferably ion exchange chromatography and affinity capture chromatography. In operation, such chromatography methods involve passing a mobile phase containing a desired molecule over an adsorbent phase, here the functionalised chromatography medium. The adsorbent phase is typically chosen such that the desired molecule is retained on it in preference to other components also present in the mobile phase.

Typically, the chromatography medium is functionalised with DEAE, Q, SP, CM, phenyl, or MEP groups, for instance DEAE, Q, SP, or CM groups. Generally, the polymer nanofibres are cellulose nanofibres and the chromatography medium is functionalised with DEAE, Q, SP, CM, phenyl, or MEP groups, for instance DEAE, Q, SP, or CM groups. Thus, the functionalised chromatography medium may comprise cellulose nanofibres derivatised with DEAE, Q, SP, CM, phenyl, or MEP groups, for instance DEAE, Q, SP, or CM groups. These ligand groups may be bonded to the polymer nanofibres and/or, where polymer chains have been covalently bonded to the nanofibres, may be bonded to the polymer chains.

The functionalised chromatography medium is typically suitable for use in an ion exchange, affinity capture, hydrophobic or mixed mode chromatography method. Thus, typically the one or more ligands groups are one or more moieties which are negatively charged, one or more moieties which are positively charged, one or more proteins, mimetic or synthetic ligands that mimic the action of protein ligands, peptides, antibodies or fragments thereof, dyes, histidine, groups containing a metal cation, or hydrophobic groups. Preferably, the one or more ligands groups are one or more moieties which are negatively charged, one or more moieties which are positively charged, one or more groups containing a metal cation, or hydrophobic groups.

As mentioned above, ligand groups may be introduced to the nanofibres/polymer chains by treating with a suitably chosen reagent. 2-chloro-N,N-diethylamine hydrochloride (DEACH) and glycidyltrimethylammonium are preferred as the reagent, particularly when the functionalised chromatography medium is for use in an anion exchange chromatography method. Other preferred reagents are 1,4-butanesulfone, sodium chloroacetate, TEMPO followed by sodium perchlorate, or allyl gycidyl ether followed by sodium disulphite, particularly when the funtionalised chromatography medium is for use in a cation exchange chromatography method. Another preferred reagent is styrene oxide, particularly when the functionalised chromatography medium is for use in a hydrophobic chromatography method.

Typically, the reagent is gycidyltrimethylammonium, 1,4-butanesulfone, or sodium chloroacetate.

Ion exchange chromatography is a technique for separating molecules or biological entities based on their ionic charge. Functionalised chromatography media for use in such methods therefore contain one or more moieties which are positively or negatively charged. Positive and/or negative charges in functionalised chromatography media are usually balanced with one or more counter ions. Ion exchange chromatography involves one or more of cation exchange chromatography and anion exchange chromatography.

Ion exchange chromatography is preferred. Thus it is preferred that the one or more ligand groups are charged (ligand) groups.

Functionalised chromatography media for use in cation exchange chromatography contain one or more moieties which are negatively charged. Typical negatively charged moieties include one or more carboxylate, sulphonate or phosphonate groups, or mixtures thereof, i.e. the moieties typically contain one or more —COO, —SO$_3^-$, or —P(OH)$_2$O$^-$ groups, or mixtures thereof. Typical functionalised chromatography media for use in cation exchange chromatography contain one or more —O—CH$_2$COO$^-$, —CH$_2$COO$^-$, —SO$_3^-$, —CH$_2$CH$_2$CH$_2$SO$_3^-$, —CH$_2$CH$_2$SO$_3^-$, or —P(OH)$_2$O$^-$ moieties.

Functionalised chromatography media for use in anion exchange chromatography contain one or more moieties which are positively charged. Typical positively charged moieties include one or more quaternary amine groups. Typical functionalised chromatography media for use in anion exchange chromatography contain one or more —N$^+$(CH$_3$)$_3$, —N$^+$(C$_2$H$_5$)H, —CH$_2$CH$_2$N$^+$(C$_2$H$_5$)H, —CH$_2$CH$_2$N$^+$(C$_2$H$_5$)$_2$(CH$_2$CH(OH)CH$_3$), —O—CH$_2$CH$_2$—N$^+$(CH$_3$)$_3$, —CH$_2$CH$_2$N$^+$(CH$_3$)$_3$, or —CH$_2$CH$_2$N$^+$(CH$_3$)$_2$H moieties.

For the avoidance of doubt, by "charged group" is meant a group that comprises a moiety that is ionised so that it bears a positive or negative charge, i.e. a "charged group" comprises an anionic or cationic moiety. A charged group is a particular example of a ligand group.

Typically, the one or more charged groups comprise one or more carboxylate (—COO$^-$), sulphonate (—SO$_3^-$), or phosphonate groups (—P(OH)$_2$O$^-$) groups, or quaternary amine groups, or mixtures thereof. Typically, the one or more charged groups comprise all anionic groups or all cationic groups, however in certain circumstances mixtures of anionic and cationic groups are envisaged. Typically, only one type of anionic group is used, but mixtures may also be used. Typically, only one type of cationic group is used, but mixtures may also be used.

Representative charged groups include —O—CH$_2$COO$^-$, —CH$_2$COO$^-$, —SO$_3^-$, —CH$_2$CH$_2$CH$_2$SO$_3^-$, —CH$_2$CH$_2$SO$_3^-$, —P(OH)$_2$O$^-$, —N$^+$(CH$_3$)$_3^-$, —N$^+$(C$_2$H$_5$)H, —CH$_2$CH$_2$N$^+$(C$_2$H$_5$)H, —CH$_2$CH$_2$N—(C$_2$H$_5$)$_2$(CH$_2$CH(OH)CH$_3$), —O—CH$_2$CH$_2$—N$^+$(CH$_3$)$_3$, —CH$_2$CH$_2$N$^+$(CH$_3$)$_3$, and —CH$_2$CH$_2$N$^+$(CH$_3$)$_2$H moieties.

Typical charged groups include DEAE, Q, SP, and CM groups. Typically, the functionalised chromatography medium is functionalised with DEAE, Q, SP, or CM groups. Thus, the functionalised chromatography medium may comprise cellulose nanofibres derivatised with DEAE, Q, SP, or CM groups.

Affinity capture chromatography is a technique for separating molecules based on their affinity to particular ligands, usually but not always biological ligands. This method may, for example, rely on the attractive forces between antibodies and antigens or enzymes and substrates. Functionalised chromatography media for use in affinity capture chromatography typically contain one or more moieties chosen from one or more proteins, peptides, antibodies or fragments thereof, dyes, histidine, or groups containing a metal cation. Functionalised chromatography media for use in affinity capture chromatography preferably contain one or more moieties chosen from groups containing a metal cation. Thus, the one or more ligand groups may comprise one or more such moieties. Alternatively, functionalised chromatography media for use in affinity capture chromatography may contain mimetic or synthetic ligands that mimic the action of protein ligands.

Typical proteins for use in affinity capture chromatography are well known to the person skilled in the art and include Protein A, Protein G and Protein L. Protein A is preferred.

Protein A is a protein well known to the skilled person. As used herein, references to "Protein A" embrace recombinant Protein A (which may have an altered sequence compared to Protein A found in *Staphylococcus aureus*) and tagged Protein A (as described in EP-B-0873353 and U.S. Pat. No. 6,399,750, the entirety of which are incorporated herein by reference).

Typical antibodies and fragments thereof for use in affinity capture chromatography are well known to the person skilled in the art and include IgG.

Typical dyes for use in affinity capture chromatography are well known to the person skilled in the art and include Yellow HE-4R, Red HE-3B and Cibacron Blue F3G.

Typical groups containing metal cations for use in affinity capture chromatography are well known to the person skilled in the art. Such groups typically contain a chelating agent to immobilize metal cations. The metal cation is typically chosen from copper, nickel, zinc and cobalt cations, preferably $Cu^{2+}$, $Ni^{2+}$, $Zn^{2+}$ and $Co^{2+}$. Hydrophobic interaction chromatography is a technique for separating molecules or biological entities based on their hydrophobicity. Functionalised chromatography media for use in such methods therefore contain one or more moieties which contain one or more hydrophobic groups. Typical hydrophobic groups include propyl, butyl, phenyl, and octyl groups.

Mixed mode (or multimodal) chromatography is a technique for separating molecules or biological entities based on two or more characteristics, typically hydrophobicity and ionic charge. This may involve a combination of hydrophobicity and anionic properties, or a combination of hydrophobicity and cationic properties. Functionalised chromatography media for use in such methods therefore typically contain one or more moieties which are positively or negatively charged, typically as defined above, and which contain one or more hydrophobic groups, typically as defined above. Positive and/or negative charges in functionalised chromatography media are usually balanced with one or more counter ions. Functionalised chromatography media for use in such methods may also contain one or more hydrophobic groups which are ionisable, for use in so-called Hydrophobic Charge Induction Chromatography (HCIC). Thus, in one embodiment, mixed mode chromatography is Hydrophobic Charge Induction Chromatography. Suitable groups for use in such methods are 4-mercapto-ethyl-pyridine (MEP) groups and octylamine groups.

Functionalised chromatography media for use in mixed mode chromatography methods which involve a combination of hydrophobic and anionic interactions contain one or more moieties which are positively charged, typically as defined above, and one or more hydrophobic groups, typically as defined above. Suitable groups for use in such methods are N-benzyl methyl ethanolamine groups and N-benzoyl-homocysteine groups. Functionalised chromatography media for use in mixed mode chromatography methods which involve a combination of hydrophobic and cationic interactions contain one or more moieties which are negatively charged, typically as defined above, and one or more hydrophobic groups, typically as defined above. Suitable groups for use in such methods are N-benzoyl-homocysteine groups.

Ligand groups are typically introduced into the functionalised chromatography medium by reacting a suitable reagent with one or more functional groups contained on the polymer nanofibres and/or polymer chains. Typical functional groups include hydroxyl, amino, halogen and carboxyl groups. In the case where the polymer nanofibres are cellulose or cellulose acetate nanofibres, the functional groups are typically hydroxyl groups.

The one or more functional groups may be activated prior to reaction with a reagent. Conventional activation methods known in the art may be employed. Thus, in the case where the functional group is an hydroxyl group, such a group may be activated by treating with carbonyl diimidazole (CDI), bisoxiranes, cyanuric acid, N-hydroxysuccinimide esters (NHS), 2-fluoro-1-methyl pyridinium toluene-4 sulphonate (FMP), $NaIO_4$, or divinylsulfone. In the case where the functional group is an amino group, such a group may be activated by treating with epichlorohydrine, glutaraldehyde or epoxide. In the case where the functional group is a carboxyl group, such a group may be activated by treating with CDI or 1-ethyl-3-(3-dimethylaminopropyl)carbodiimide (EDC). In the case where the functional group is a halogen atom, such a group may be activated by treating with divinylsulfone.

A skilled person can choose suitable reagents to introduce particular groups and moieties onto particular nanofibres/polymer chains, for example on the basis of the desired ligand groups and moieties and the functional groups contained in those nanofibres/polymer chains. Typical reagents include 2-chloro-N,N-diethylamine hydrochloride (DEACH), glycidyltrimethylammonium chloride (GMAC), 1,4-butanesulfone, or sodium chloroacetate.

Typically,
the chromatography method is a cationic exchange method, and the chromatography medium is functionalised with one or more charged groups comprising one or more carboxylate, sulphonate or phosphonate moieties; or the chromatography method is an anionic exchange method, and the chromatography medium is functionalised with one or more charged groups comprising one or more quaternary amino or diethylaminemoieties;

the chromatography method is an affinity capture chromatography method, and the chromatography medium is functionalised with one or more groups containing a metal cation;

the chromatography method is a hydrophobic interaction chromatography method, and the chromatography medium is functionalised with one or more propyl, butyl, phenyl, or octyl groups; or the chromatography method is a mixed mode chromatography method, and the chromatography medium is functionalised with one or more MEP, octylamine, N-benzyl methyl ethanolamine or N-benzoyl-homocysteine groups.

Properties of Functionalised Chromatography Medium

The density of ligand groups in the functionalised chromatography medium is typically 100-1,500 µmol/g of functionalised chromatography medium. The density is preferably 300-1,500 mol/g, more preferably 500-1200 mol/g, even more preferably 600-1000 µmol/g, even more preferably 700-900 µmol/g. In some embodiments, the density is 100-500 mol/g. When the ligand groups are charged groups, this figure represents the charge density of the material.

The density is typically determined by a titration method to determine the number of moieties in the functionalised material. A skilled person will be aware of suitable methods to use to determine the amount of particular moieties present in a given sample of functionalised material.

In the context of functionalisation with trimethylammonium chloride, the density can be determined as the trimethylammonium chloride density which may be determined by the following assay:

1) Washing 50 mg of material with 100 mL 0.1M HCL solution on a Buchner filter funnel and then with a further 100 mL 0.01M HCl solution;

2) Drying the material in a drying oven at 75° C. to constant mass before tearing into small pieces and placing in a 50 mL centrifuge tube equipped with a small magnetic stir bar;

3) Adding 15 mL deionised water along with approximately 1 mL (added via a teat pipette) potassium chromate solution which causes the mixture to become yellow in colour;

4) Stirring the mixture was vigorously for 20 minutes before being titrating with 0.1M silver nitrate, the endpoint of the titration being identified by a change in colour from clear yellow to misty brown;
5) Calculating the trimethylammonium chloride content (μmol/g) as the number of micromoles of silver nitrate added to reach end point/number of grams of nanofibre material used in the titration.

In the context of functionalisation with sulfonic acid (S) groups, the density can be determined as the sulfonic acid density which may be determined by the following assay:
1) Washing a dried sample of functionalised material with 0.1M HCL and 0.01M HCl;
2) Drying the material in an oven and weighing;
3) Determining the molarity of the material by the amount of NaOH that must be added to reach pH7;
4) Calculating the sulfonic acid (S) content (μmol/g) as the number of micromoles of NaOH added to reach pH7/number of grams of nanofibre material used in the titration.

The functionalised chromatography material typically has a dynamic binding capacity (DBC) of 10 to 210 mg/mL (10% breakthrough), preferably 20 to 195 mg/mL (10% breakthrough), 30 to 180 mg/mL (10% breakthrough), 40 to 165 mg/mL (10% breakthrough), or 50 to 150 mg/mL (10% breakthrough). In certain embodiments, the DBC may be up to 50 mg/mL (10% breakthrough), for instance 10 to 50 mg/mL (10% breakthrough). For anionic functionalised chromatography media, the DBC (10% breakthrough) is typically calculated as the DBC (10% breakthrough) for BSA. For cationic functionalised chromatography media, the DBC (10% breakthrough) is typically calculated as the DBC (10% breakthrough) for lysozyme.

The DBC for 10% breakthrough can be determined in accordance with standard means, e.g. using an AKTA Pure system.

DBC for 10% breakthrough is typically determined according to the following assay method:
1) Loading material (For anion exchange material the loading material was 1 mg/mL BSA in 10 mM Tris to pH 8. For cation exchange material the loading material was 1 mg/mL lysozyme in sodium acetate pH 4.7 10 mM.) is passed through functionalised material contained within a holder on an AKTA Pure system (GE Healthcare);
2) material is loaded under a determined membrane volume per minute flowrate (mV/min) until the concentration after the holder outlet exceeded 10% of that loaded as determined by the UV flow cell;
3) Accounting for dead volumes in the system and the holder device the total amount of protein loaded onto the disc at the 10% breakthrough was determined through analysis of the chromatogram in the Unicorn software (GE Healthcare).

Typically, the functionalized chromatography material is a salt intolerant material. A salt intolerant material is a material which is capable of eluting a product in the elute step of a bind elute separation process at a low salt concentration. As used here, a low salt concentration is a solution having a conductivity of less than 10 mS/cm.

Chromatography Process

The process of the present invention is a chromatographic separation process. Typically the chromatographic separation is a bind-elute chromatographic separation process. Alternatively, the chromatographic separation process is a flow-through chromatographic separation process. The functionalised chromatography medium is used as the stationary phase in the chromatographic separation process.

The process of the present invention involves contacting a composition comprising a viral product as defined herein and product-related impurities as defined herein with a functionalised chromatography medium as defined herein. Alternatively, the process of the present invention involves contacting a composition comprising a viral product as defined herein and non-product-related impurities as defined herein with a functionalised chromatography medium as defined herein.

The functionalised chromatography medium may be in the form of a membrane or a sheet. Such membranes and sheets are suitable for use in membrane chromatography methods. Membrane chromatography methods are well known to the person skilled in the art and are discussed in "Membrane Processes in Biotechnologies and Pharmaceutics" ed. Catherine Charcosset, Elsevier, 2012, the entirety of which is incorporated herein by reference.

The functionalised chromatography medium may be housed in a chromatography cartridge or holder. The terms cartridge and holder are used synonymously herein. The cartridge typically comprises one or more functionalised chromatography media of the present invention. The cartridge is typically cylindrical.

Typically, the chromatography cartridge comprises one or more functionalised chromatography media of the present invention stacked or wound inside a typically cylindrical holder. The chromatography cartridge may be designed to operate under axial or radial flow. In one embodiment, the cartridge comprises one or more functionalised chromatography media of the present invention wound inside a holder, which is designed to operate under axial flow. Alternately, the cartridge comprises one or more functionalised chromatography media of the present invention stacked inside a holder, which is designed to operate under radial flow.

Typically, the chromatography cartridge comprises two or more functionalised chromatography media of the present invention. The chromatography cartridge typically comprises up to twenty functionalised chromatography media of the present invention.

Typically, the chromatography cartridge also comprises one or more frits within the typically cylindrical holder. Frits are well known to the person skilled in the art and refer to rigid porous structures, typically rigid metal, polymeric or ceramic, preferably rigid metal or ceramic, porous structures. Frits are typically included in a chromatography cartridge to improve flow distribution through the cartridge and/or to support the one or more functionalised chromatography media of the present invention. Pores in typical frits have diameters from 1 to 1000 μm, preferably from 5 to 500 μm, more preferably from 10 to 150 μm. Other suitable frit pore diameters include from 1 to 20 μm, preferably from 5 to 10 μm, more preferably from 3 to 7 μm.

Typically, the cartridge comprises two or more functionalised chromatography media of the present invention and one or more frits, the frits being located between functionalised chromatography media.

In some embodiments, the cartridge does not comprise frits.

The cartridge may comprise alternative spacer materials instead of or in addition to frits. Typical alternative spacer materials include non-woven and woven materials.

Non-woven materials, e.g. non-woven polymer materials, are known to the person of skill in the art. Such non-woven materials are porous, i.e. allow the passage of liquid, typically without significant pressure drop. Typically, the non-woven polymer material is polypropylene. Typically, the non-woven material has an area density of 45-150 gsm.

In some embodiments, the cartridge comprises two or more functionalised chromatography media of the present invention and one or more non-woven polymer material layers as defined above, the one or more non-woven polymer material layers being located between functionalised chromatography media.

Woven materials are known to the person of skill in the art. Such woven materials are porous, i.e. allow the passage of liquid, typically without significant pressure drop. Typically, the woven material is a woven polymer material, preferably woven polypropylene. Typically, the woven material has a thickness less than 1 mm.

Typically, the chromatography cartridge also comprises one or more inlet fluid distribution means and/or outlet fluid collection means. Such means are well known to the person skilled in the art.

The process of the invention involves contacting the composition defined herein with a functionalised chromatography medium as defined herein, which may be in the form of a membrane or sheet as defined herein, and/or contained in a cartridge as defined herein. The viral product and product-related impurities are thought to bind to the functionalised chromatography medium with varying strengths. Typically, this allows their separation in a subsequent elution step. This can be carried out in accordance with conventional methods known for the bind and elute phases of known chromatographic methods. Alternatively, the differing binding strengths of the viral product and product-related impurities enables the viral product to be separated from product-related impurities in a flow-through mode, i.e. the composition comprising the viral product and product-related impurities is contacted with the functionalised chromatography medium and the viral product is eluted from the column whilst the product-related impurities substantially bind to the functionalised chromatography medium.

Alternatively or in addition, the viral product and non-product-related impurities are thought to bind to the functionalised chromatography medium with varying strengths. Typically, this allows their separation in a subsequent elution step. This can be carried out in accordance with conventional methods known for the bind and elute phases of known chromatographic methods. Alternatively, the differing binding strengths of the viral product and non-product-related impurities enables the viral product to be separated from non-product-related impurities in a flow-through mode, i.e. the composition comprising the viral product and non-product-related impurities is contacted with the functionalised chromatography medium and the viral product is eluted from the column whilst the non-product-related impurities substantially bind to the functionalised chromatography medium.

The composition comprises the viral product and product-related impurities as defined herein typically in a mobile phase. Alternatively, the composition comprises the viral product and non-product-related impurities as defined herein typically in a mobile phase. The mobile phase is typically an aqueous phase, preferably a buffered solution, e.g. buffered saline, or a Tris buffer. The composition is typically obtained from a process used to produce the viral product or after a buffer exchange step, e.g. a viral vector production process. Such processes are known to one of skill in the art (Urabe et al., 2006) (Qu et al., 2007) (M. Lock et al., 2012) (Lee et al., 2009) all of which are incorporated herein by reference.

The composition typically also comprises additional by-products of the process used to produce the viral product. The additional by-products may include e.g. buffer, cell debris, cell proteins, cell DNA and components of the cell culture medium.

Prior to processing in accordance with the present invention, additional processing steps may be carried out, e.g. one or more of centrifugation, treatment with DNAse, size exclusion chromatography, affinity chromatography and/or ionic exchange chromatography.

The present invention accordingly provides a process for recovering a viral product, which process comprises:
(i) providing a composition as defined herein comprising a viral product as defined herein and product-related impurities as defined herein,
(ii) optionally subjecting the composition to one or more processing steps chosen from centrifugation, treatment with DNAse, size exclusion chromatography, affinity chromatography and ionic exchange chromatography, and
(iii) contacting the resultant composition with a functionalised chromatography medium as defined herein.

Alternatively, the present invention accordingly provides a process for recovering a viral product, which process comprises:
(i) providing a composition as defined herein comprising a viral product as defined herein and non-product-related impurities as defined herein,
(ii) optionally subjecting the composition to one or more processing steps chosen from centrifugation, treatment with DNAse, size exclusion chromatography, affinity chromatography and ionic exchange chromatography, and
(iii) contacting the resultant composition with a functionalised chromatography medium as defined herein.

In some embodiments, step (ii) involves at least affinity chromatography.

Step (i) typically involves a viral vector production process, which may be carried out in accordance with known methods, as discussed elsewhere.

The composition typically has a dissolved salt concentration such that the electrical conductivity is below 30 mS/cm. The conductivity is preferably below 25 mS/cm, more preferably below 20 mS/cm, even more preferably below 15 mS/cm, even more preferably below 10 mS/cm, even more preferably below 9 mS/cm, even more preferably 8 mS/cm or below. A skilled person is well aware of suitable methods that can be used to determine electrical conductivity.

The process of the present invention may involve contacting the composition with the functionalised chromatography medium in a batch process, i.e. placing the composition and medium in a vessel, or in a continuous process, i.e. wherein the functionalised chromatography medium is in the form of a membrane or sheet and the composition is passed through a holder or cartridge comprising one or more said membranes/sheets and optionally one or more frits or other spacer materials as defined herein. Typically in such embodiments, the composition is passed through the holder such that (a) the path length through said one or more membranes/sheets is less than 2 mm and/or (b) the total path length through membranes, sheets frits and other spacer materials present in the holder is less than 50 mm.

In embodiment (a) it should be understood that the composition may also pass through other materials in the holder which are not the membranes/sheets, and the 2 mm path length does not include these other materials. In embodiment (b), the 50 mm path length includes other materials in the holder. For the avoidance of doubt, neither of the path lengths mentioned above include any air gaps between layers of material in the holder.

The processes of the present invention can be operated at high flowrates. Thus, typically in the chromatography process of the present invention, the composition is contacted with the functionalised chromatography medium for a period of time of one minute or less, preferably 50 seconds or less, more preferably 40 seconds or less, yet more preferably 30 seconds or less, still more preferably 20 seconds or less, or even 15 seconds or less, 12 seconds or less, 10 seconds or less, 8 seconds or less, 6 seconds or less, 4 seconds or less, 2 seconds or less, 1.5 seconds or less, or even 1 second or less.

The process of the invention typically comprises a further step of recovering the viral product from the functionalised chromatography medium. The viral product becomes adsorbed on the functionalized chromatography medium when contacted with the functionalised chromatography medium. This step can typically be effected by contacting the functionalised chromatography medium to which is adsorbed the one or more biological molecules with an elution buffer. Typically this involves contacting with a liquid phase of increasing ionic strength with respect to time. This selectively elutes the viral product. Product-related impurities may also be adsorbed to the functionalised chromatography medium. Non-product-related impurities may also be adsorbed to the functionalised chromatography medium. The viral product may be selectively eluted in preference to these impurities by careful incremental control of the ionic strength of the elution buffer. This can be carried out in accordance with conventional methods known for the elute phase of such chromatographic methods. Thus, the process is typically a bind-elute chromatographic method.

Between the bind and elute steps, the process may further comprise a step of washing the functionalised chromatography medium to which is adsorbed the viral product and/or product-related and/or non-product-related impurities. This washing step is carried out to remove any components which are not bound to the functionalised chromatography medium or chromatography cartridge. This can be carried out in accordance with conventional methods known for the washing phase of such chromatographic methods. This washing step typically involves washing with a liquid phase of low ionic concentration.

Typically, the process of the invention comprises the steps of:
(i) contacting the composition as defined herein with the functionalised chromatography medium as defined herein;
(ii) optionally washing the functionalised chromatography medium with a liquid phase of low ionic concentration; and
(iii) selectively eluting the viral product and the product-related impurities by contacting the functionalised chromatography medium with a liquid phase of increasing ionic strength.

Alternatively, the process of the invention comprises the steps of:
(i) contacting the composition as defined herein with the functionalised chromatography medium as defined herein;
(ii) optionally washing the functionalised chromatography medium with a liquid phase of low ionic concentration; and
(iii) selectively eluting the viral product and the non-product-related impurities by contacting the functionalised chromatography medium with a liquid phase of increasing ionic strength.

After the elute step, the process may further comprise a step of regenerating the functionalised chromatography medium. Typically this is effected by contacting the functionalised chromatography medium from which the viral product and/or product related impurities have been eluted with buffer. This can be carried out in accordance with conventional methods known for the regeneration phase of such chromatographic methods.

Alternatively, the viral product does not become adsorbed on the functionalised chromatography medium when contacted with the functionalised chromatography medium. Instead, the product-related impurities may become adsorbed on the functionalised chromatography medium when contacted with the functionalised chromatography medium. Thus, by flowing a solution comprising the composition comprising the viral product and the product-related impurities through a cartridge comprising the functionalised chromatography medium, it is possible to selectively collect the viral product in preference to the product-related impurities, as the product-related impurities remain substantially bound to the functionalised chromatography medium after completion of the flow-through step.

Alternatively or in addition, the non-product-related impurities may become adsorbed on the functionalised chromatography medium when contacted with the functionalised chromatography medium. Thus, by flowing a solution comprising the composition comprising the viral product and the non-product-related impurities through a cartridge comprising the functionalised chromatography medium, it is possible to selectively collect the viral product in preference to the non-product-related impurities, as the non-product-related impurities remain substantially bound to the functionalised chromatography medium after completion of the flow-through step.

Thus, the process of the invention alternatively comprises the steps of:
(i) contacting a solution comprising the composition as defined herein with the functionalised chromatography medium as defined herein; and
(ii) collecting the solution that has contacted the functionalised chromatography medium in step (i), which solution comprises the viral product.

Typically, the process of recovering a viral product in accordance with the present invention comprises a single bind-elute step or a single flow-through step. Alternatively, the process in accordance with the present invention may comprise more than one bind-elute step in series, e.g. two, three, four, five or more bind-elute steps. Alternatively, the process in accordance with the present invention may comprise more than one flow-through step in series, e.g. two, three, four, five or more flow-through steps. Alternatively, the process in accordance with the present invention may comprise a combination of bind-elute and flow-through steps in series, e.g. two, three, four, five or more steps in total.

Typically, the viral product is recovered and the product-related impurities discarded. Typically, the non-product-related impurities are discarded. Certain product-related impurities may, though, have use in certain applications, so it is also envisaged that the product-related impurity may be collected as a secondary product.

The process of the invention is for recovering a viral product. However, it should be understood that no chromatographic process is capable of providing a viral product in 100% purity. Thus, the present invention provides a means for recovering from a composition comprising a viral product and product related impurities a product fraction that is enriched in viral product compared with the original composition. Thus, typically, the product fraction contains a greater amount of viral product expressed as a percentage of the total amount of viral product and product-related impurities than was present in the composition. Typically, the amount of viral product in the product fraction expressed as a percentage of the total amount of viral product and product-related impurities is greater than the amount in the composition by a factor of 10 or more times, preferably 100, 1000, 10000, 1×10^5, 1×10^6, 1×10^7, 1×10^8, 1×10^9, 1×10^10, 1×10^11, 1×10^12, 1×10^13, or 1×10^14 or more times.

Thus, typically, the amount of viral product in the product fraction expressed as a percentage of the total amount of viral product and product-related impurities is denoted by % PF, which can be calculated by $100PF_{VP}/(PF_{VP}+PF_I)$, where $PF_{VP}$ is the amount of viral product in the product fraction, and $PF_I$ is the amount of product-related impurities in the product fraction. The amount of viral product in the original composition expressed as a percentage of the total amount of viral product and product-related impurities can be denoted by % C, which is calculated as $100C_{VP}/(C_{VP}+C_I)$, where $C_{VP}$ is the amount of viral product in the composition, and $C_I$ is the amount of product-related impurities in the composition.

The process of the invention enriches the amount of viral product in the product fraction relative to the amount in the composition such that typically % PF≥10% C. Preferably, % PF≥100% C, 1000% C, 10000% C, % C×10^5, % C×10^6, % C×10^7, % C×10^8, % C×10^9, % C×10^10, % C×10^11, % C×10^12, % C×10^13, or % C×10^14.

Typically, the process of the present invention employs a simulated or actual moving bed system. Thus typically, the process comprises introducing the composition into one or more simulated or actual moving bed chromatography apparatuses having a plurality of linked chromatography columns, which chromatography columns contain as adsorbent the functionalised chromatography medium.

Any known simulated or actual moving bed apparatus may be used to carry out the chromatographic process, provided that it comprises, as adsorbent, the functionalised chromatography medium.

Simulated and actual moving bed chromatography are known techniques, familiar to those of skill in the art. The principle of operation involves countercurrent movement of a liquid eluent phase and a solid adsorbent phase. This operation allows minimal usage of solvent making the process economically viable. Such separation technology has found applications in diverse areas including purification of biological molecules using membrane adsorbents.

A simulated moving bed system consists of a number of individual columns containing adsorbent which are connected together in series. Eluent is passed through the columns in a first direction. The injection points of the feedstock and the eluent, and the separated component collection points in the system are periodically shifted by means of a series of valves. The overall effect is to simulate the operation of a single column containing a moving bed of the solid adsorbent. Thus, a simulated moving bed system consists of columns which, as in a conventional stationary bed system, contain stationary beds of solid adsorbent through which eluent is passed, but in a simulated moving bed system the operation is such as to simulate a continuous countercurrent moving bed.

An actual moving bed system is similar in operation to a simulated moving bed system. However, rather than shifting the injection points of the feed mixture and the eluent, and the separated component collection points by means of a system of valves, instead a series of adsorption units (i.e. columns) are physically moved relative to the feed and drawoff points. Again, operation is such as to simulate a continuous countercurrent moving bed.

The present inventors have found that using a functionalised chromatography medium as outlined above has several advantages compared with prior art viral vector purification processes.

One advantage is that the material is relatively intolerant to salt, and it is therefore possible to elute the viral product from the chromatography medium using an elution buffer of relatively low salt concentration. This low salt concentration can be measured by the conductivity of the elution buffer.

The present invention therefore also provides a process for recovering a viral product as defined herein from a composition as defined herein, comprising said product and product-related impurities as defined herein, which process comprises contacting the composition with a salt intolerant chromatography medium, wherein the salt intolerant chromatography medium is capable of eluting the viral product at a conductivity of less than 10 mS/cm.

Alternatively, the present invention also provides a process for recovering a viral product as defined herein from a composition as defined herein, comprising said product and non-product-related impurities as defined herein, which process comprises contacting the composition with a salt intolerant chromatography medium, wherein the salt intolerant chromatography medium is capable of eluting the viral product at a conductivity of less than 10 mS/cm.

In these embodiments, the salt intolerant chromatography medium is a salt intolerant material as defined above.

The salt intolerant chromatography medium is similar in many respects to the functionalised chromatography medium defined above, but it is not restricted to chromatography media comprising polymer nanofibres. However, the salt intolerant chromatography medium is typically a polymeric medium formed of one or more of the polymers defined above (for the polymer nanofibres). The salt intolerant chromatography medium is also typically a functionalised medium, functionalised with one or more ligand groups as defined above.

A further advantage is that only a low volume of chromatography material needs to be used to separate packed from unpacked vectors.

The present invention therefore also provides a process for recovering a viral product as defined herein from a composition as defined herein, comprising said product and product-related impurities as defined herein, which process comprises contacting the composition with a chromatography medium in the form of a membrane or sheet and the composition is passed through a holder comprising one or more said membranes or sheets and optionally one or more frits or other spacer materials, wherein the composition is passed through the holder such that (a) the path length through said one or more membranes or sheets is less than 2 mm or (b) the total path length through membranes, sheets, frits and other spacer materials is less than 50 mm.

In this embodiment, the chromatography medium is similar in many respects to the functionalised chromatography medium defined above, but it is not restricted to chromatography media comprising polymer nanofibres. However, the chromatography medium is typically a polymeric medium formed of one or more of the polymers defined above (for the polymer nanofibres). The chromatography medium is also typically a functionalised medium, functionalised with one or more ligand groups as defined above.

A further advantage is that short residence times are possible.

The present invention therefore also provides a process for recovering a viral product as defined herein from a composition as defined herein, comprising said product and product-related impurities as defined herein, which process comprises contacting the composition with a chromatography medium in the form of a membrane or sheet and the composition is passed through a holder comprising one or more said membranes or sheets and optionally one or more frits or other spacer materials, wherein the composition is contacted with the chromatography medium for a period of time of one minute or less.

In this embodiment, the chromatography medium is similar in many respects to the functionalised chromatography medium defined above, but it is not restricted to chromatography media comprising polymer nanofibres. However, the chromatography medium is typically a polymeric medium formed of one or more of the polymers defined above (for the polymer nanofibres). The chromatography medium is also typically a functionalised medium, functionalised with one or more ligand groups as defined above.

Preferred residence (contact) times are as defined above.

A further advantage is that it is thought that the process according to the present invention ensures that a greater proportion of the viral particles remain intact during the chromatographic separation step than when alternative purification processes are used. Thus, carrying out the process according to the present invention is thought to damage the viral particles less than carrying out viral purification processes that are known in the prior art.

Viral Products, Impurities, Compositions and Uses

The present invention provides a viral product obtained or obtainable by the process of the present invention. In a preferred embodiment, the present invention provides a viral vector obtained or obtainable by the process of the present invention. Such products may advantageously be used in the microbial treatment, vaccination and gene therapy methods of the invention.

Also provided is a product-related impurity obtainable or obtained by the process of the present invention. Although such impurities will usually be discarded, in certain embodiments they may be useful in therapy e.g. vaccination.

Also provided is a composition comprising a viral product as defined herein in association with a pharmaceutically acceptable carrier or diluent. Such compositions can be used in the microbial treatment, vaccination and gene therapy methods of the invention.

Also provided is a composition comprising a product-related impurity as defined herein in association with a pharmaceutically acceptable carrier or diluent.

Preferred compositions are free of contamination microorganisms and pyrogens.

The viral products (and optionally product-related impurities) of the invention may be administered in a variety of dosage forms. Thus, they can be administered orally, for example as aqueous or oily suspensions. They may also be administered parenterally, either subcutaneously, intravenously, intramuscularly, intrasternally, transdermally or by infusion techniques. They may also be administered by inhalation in the form of an aerosol via an inhaler or nebuliser.

The formulations for oral administration, for example, may contain, together with the active ingredient, solubilising agents, e.g. cyclodextrins or modified cyclodextrins; diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations.

Liquid dispersions for oral administration may be solutions, syrups, emulsions and suspensions. The solutions may contain solubilising agents e.g. cyclodextrins or modified cyclodextrins. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol; solubilising agents, e.g. cyclodextrins or modified cyclodextrins, and if desired, a suitable amount of lidocaine hydrochloride.

Solutions for intravenous or infusions may contain as carrier, for example, sterile water and solubilising agents, e.g. cyclodextrins or modified cyclodextrins or preferably they may be in the form of sterile, aqueous, isotonic saline solutions.

The viral products of the present invention are useful for in vivo delivery of therapeutic genetic material to a patient, in carrying out gene therapy or genetic-vaccination treatment for example, wherein the viral product includes therapeutic genetic material. It will be understood that the term "therapeutic genetic material" is used herein to denote any genetic material or nucleic acid administered for obtaining a therapeutic effect, e.g. by expression of therapeutically useful proteins or RNA's. Such methods may optionally involve also administering one or more product-related impurities to a patient, particularly in the case of vaccination.

Gene therapy has applications across the whole field of human disease including, but not limited to, the treatment of cancer (including locally accessible tumour nodules suitable for direct injection, as well as metastatic cancer requiring systemic treatment), Parkinson's disease, X-SCID, Sickle Cell Disease, Lesch-Nyhan syndrome, phenylketonuria (PKU), Huntington's chorea, Duchenne muscular dystrophy, hemophilia, cystic fibrosis, lysosomal storage diseases, cardiovascular diseases and diabetes.

The viral products of the invention may also be used for the delivery of viral vaccines. Vaccination against HIV, tuberculosis, malaria, flu, cancer and other diseases are envisaged. Vaccines may be given in prime boost regimes (i.e. by multiple administrations) or in combination with adjuvants.

The viral products of the present invention are useful for in vivo delivery of therapeutic agents to a patient, in carrying out microbial therapy including virotherapy for example.

In certain embodiments, the viral product of the present invention may be used in combination with other medicaments, e.g. other medicaments effective in the treatment of cancer.

The viral product may also be used in an ex-vivo method of inserting a polynucleotide into a cell, which method comprises contacting the cell with a viral product of the invention ex-vivo. Such ex-vivo methods may, for instance, involve ex-vivo manipulation of cells for subsequent use in therapy. Typical therapeutic applications include Chimeric antigen receptor-T (CAR-T) cancer therapy.

Alternatively, the ex-vivo methods may be used for research purposes, or for e.g. gene editing (including CRISPR) for instance in the production of a transgenic crop or enzyme for the production of a biofuel.

Cells modified in accordance with this ex-vivo method may subsequently be administered to a patient as a therapeutic. The present invention provides a cell obtained or obtainable by an ex-vivo method of the present invention. The present invention therefore also provides a method of treatment which comprises administering to a patient in need thereof one or more cells modified in accordance with an ex-vivo method of the invention. Also provided is one or more cells which have been modified in accordance with an ex-vivo method of the invention for use in a method of treating the human or animal body by therapy, for instance in the treatment of cancer.

The following Examples illustrate the invention.

EXAMPLES

Materials and Equipment

Unless otherwise noted all chemicals were obtained from, or are available from, companies such as Fisher Scientific, Sigma-Aldrich, FluoroChem, Repligen, and VWR.

Washing Protocols

Washing Protocol A

The reaction media was replaced with an equal volume de-ionised water and circulated for 1 hour. The rinsing procedure was repeated once more. Finally, the materials were treated with an equal volume of aqueous ethanol (2:1-$H_2O$:EtOH) before being removed from the reaction vessel.

Washing Protocol B

The reaction media was replaced with an equal volume of de-ionised water and circulated for 1 hour. After this time, the washing media was replaced with 0.01M HCl which was circulated for 1 hour whereupon it was replaced with 0.001M HCl and circulated for 1 hour. Finally, the media was replaced with 2:1 mixture of $H_2O$:EtOH which was circulated for 1 hour. The derivatised nanofibres were then removed from the reaction vessel.

Washing Protocol C

The reaction media was replaced with an equal volume of 1:1 mixture of warm (60° C.) de-ionised water:acetone which was circulated for 30 mins. The washing procedure was repeated twice more. Finally, the media was replaced with 2:1 mixture of $H_2O$:EtOH which was circulated for 1 hour. The derivatised nanofibres were then removed from the reaction vessel.

Washing Protocol D

2 Ltrs of ultrapure water was pumped through the nanofibre material.

Washing Protocol E

The reaction media was replaced with an equal volume of 1:1-de-ionised water:EtOH and circulated for 1 hour. The washing procedure was repeated twice more. Finally, the media was replaced with 2:1 mixture of $H_2O$:EtOH which was circulated for 1 hour. The derivatised nanofibres were then removed from the reaction vessel. Finally, the media was replaced with 2:1 mixture of $H_2O$:EtOH which was circulated for 1 hour. The derivatised nanofibres were then removed from the reaction vessel.

Washing Protocol F

The reaction media was replaced with ultapure de-ionised water. The nanofibre materials were gently stirred in the clean water for 30 mins. After this time, the washing media was replaced and the wash cycle repeated.

Washing Protocol G

The reaction media was poured out and the beaker was replenished with water until the pH of the effluent was neutral or slightly acidic.

I Preparation of Materials

Preparative Example 1

A solution of cellulose acetate, with a relative molecular mass of 29,000 g/mol, was dissolved in common solvents prior to electrospinning to produce fibres with diameters ranging between 300-600 nm. Optimised conditions for nanofibre production can be found in, for example, O. Hardick, et al, J. Mater. Sci. 46 (2011) 3890, the entirety of which is incorporated herein by reference. Sheets of approximately 20 g/m² material were layered and subjected to a combined heating and pressure treatment.

Reference Example 1—Trimethylammonium Chloride Functionalization

Nanofibre materials were derivatised according the scheme outlined below:

Step (i): Saponification of Cellulose Acetate (CA) to Regenerated Cellulose (RC)

Cellulose acetate sheets (44*32 mm*150 mm) obtained in accordance with the method of Preparative Example 1 were placed into a large beaker containing 5 L of a 0.075M sodium hydroxide solution in 2:1-water:ethanol. The reaction mixture was circulated at room temperature for 48 hours. The materials were then washed according to washing protocol A.

Step (ii): Glycidyltrimethylammonium Chloride Derivatisation

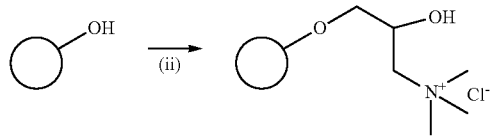

Materials obtained in step (i) were suspended in 1 Ltr 0.5M NaOH. The reaction media was circulated for 15 minutes prior to the addition of glycidyltrimethylammonium chloride (25 mL, 100 mL) in a single portion. The reaction media was circulated for a further 16 hours at room temperature. The materials were then washed according to washing protocol B.

The trimethylammonium chloride content was determined by the following method. 50 mg of material was washed with 100 mL 0.1M HCl solution on a Buchner filter funnel and then with a further 100 mL 0.01M HCl solution. The material was then placed in a drying oven at 75° C. and dried to constant mass before being torn into small pieces and then placed in a 50 mL centrifuge tube. A small magnetic stir bar and 15 mL deionised water were then added along with approximately 1 mL (added via a teat pipette) potassium chromate solution which caused the mixture to become yellow in colour. The mixture was stirred vigorously for 20 minutes before being titrated with 0.1M silver nitrate. The endpoint of the titration is identified by a change in colour from clear yellow to misty brown.

The trimethylammonium chloride content (μmol/g) was calculated as the number of micromoles of silver nitrate added to reach end point/number of grams of nanofibre material used in the titration.

The trimethylammonium chloride content (μmol/g) of the sample treated with 25 mL GMAC was found to be 308. The trimethylammonium chloride content (μmol/g) of the sample treated with 100 mL GMAC was found to be 775.

Preparative Example 3—Glycidol/Trimethylammonium Chloride Functionalization

Nanofibre materials were derivatised according the scheme outlined below:

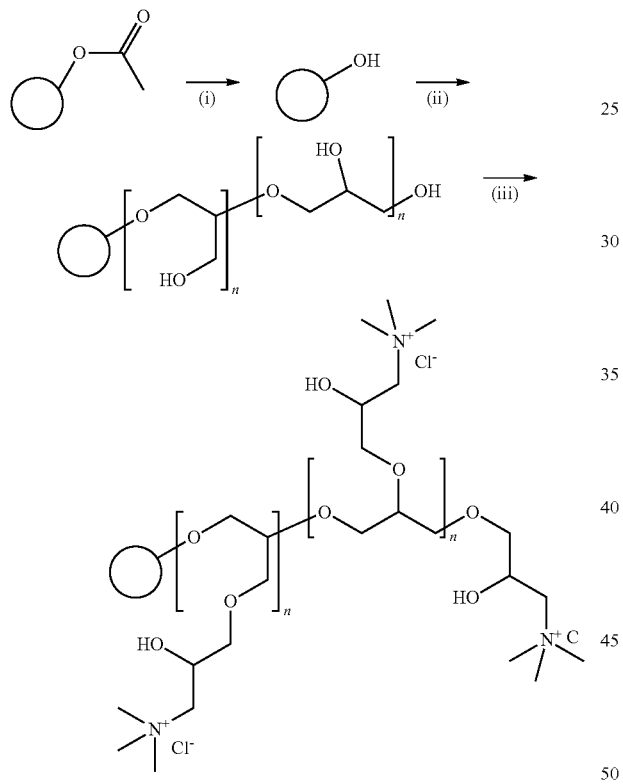

Step (i): Saponification of Cellulose Acetate (CA) to Regenerated Cellulose (RC)

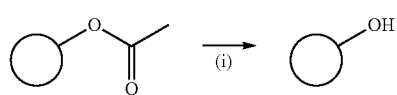

Cellulose acetate sheets (44*32 mm*150 mm) obtained in accordance with the method of Preparative Example 1 were placed into a large beaker containing 5 L of a 0.075M sodium hydroxide solution in 2:1-water:ethanol. The reaction mixture was stirred at room temperature for 48 hours. The materials were then washed according to washing protocol A.

Step (ii): Glycidol Polymerisation

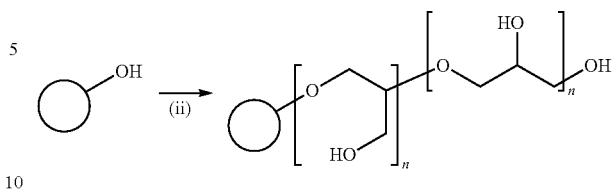

Materials from (i) were suspended in 1 L of 0.5M NaOH. The reaction media was circulated for 15 minutes prior to the careful addition of Glycidol (180 mL) in a single portion. The reaction media was circulated at room temperature for 16 hours and the material was subsequently washed according to washing protocol B.

Step (iii): Glycidyltrimethylammonium Chloride Derivatisation

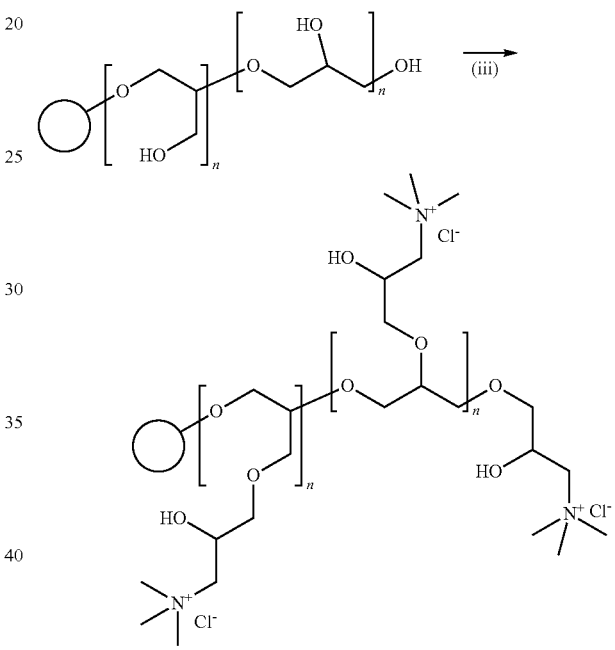

Materials obtained in step (ii) were typically suspended in 1 Ltr 0.5M NaOH. The reaction media was circulated for 15 minutes prior to the addition of glycidyltrimethylammonium chloride (5 mL, 100 mL) in a single portion. The reaction media was circulated for a further 16 hours at room temperature. The materials were then washed according to washing protocol C.

The trimethylammonium chloride content was determined using the method from Preparative Example 2.

The trimethylammonium chloride content (μmol/g) of the sample treated with 50 mL GMAC was found to be 523. The trimethylammonium chloride content (μmol/g) of the sample treated with 100 mL GMAC was found to be 775.

Preparative Example 4—Preparation of Adenovirus (AV) Vectors

Adenovirus vectors were prepared by analogy with known methods.

Thus, adenovirus vectors were produced in HEK-293 cell culture. Adenovirus vector production methods are discussed in Volume 1: Adenoviruses, Ad Vectors, Quantitation, and Animal Models Editors: William S. M. Wold, Ann E. Tollefson ISBN: 978-1-58829-598-9 (Print) 978-1-59745-166-6 (Online). The cells were lysed using freeze thaw cycles, and the resultant material purified using centrifugation, followed by treatment with DNAse (benzonase) (Wright et al., 2005) The resultant material was dialysed into 10 mM Tris buffer.

Preparative Example 5—Preparation of Adenoassociated Virus (AAV) Vectors

Adenoassociated virus vectors containing a payload consisting of a sequence of DNA encoding for green florescent protein (GFP) were prepared by analogy with known methods.

Thus, adeno-associated virus vectors were produced in HEK-293 cell culture (Martin Lock et al., 2010). The cells were lysed, and the resultant material purified using filtration, followed by treatment with DNAse (benzonase) (Wright et al., 2005). and subsequent size exclusion chromatography (Chromatographic purification of recombinant adenoviral and adeno-associated viral vectors: methods and implications; Gene Therapy (2005) 12, S5-S17. doi: 10.1038/sj.gt.3302611; http://www.nature.com/gt/journal/v12/n1s/full/3302611a.html). The resultant material was dialysed into Bis Tris Propan 10 mM pH 8.

Preparative Example 6—Alternative Preparation of Adenoassociated Virus (AAV) Vectors Adenoassociated virus vectors containing a payload consisting of a sequence of DNA encoding for green florescent protein (GFP) were prepared by analogy with known methods as discussed above.

Thus, adeno-associated virus vectors were produced in HEK-293 cell culture. The cells were lysed, and the resultant material purified using filtration (0.45 µm, 0.22 µm). The resultant material was dialysed into Bis Tris Propan 10 mM pH 8.

II Analysis of Materials

Analytical Example 1—DBC of Chromatographic Materials

Loading material was passed through a selected functionalised nanofibre disc contained within a holder on an AKTA Pure system (GE Healthcare). The material was loaded under a determined membrane volume per minute flowrate (mV/min) until the concentration after the holder outlet exceeded 10% of that loaded as determined by the UV flow cell. Accounting for dead volumes in the system and the holder device the total amount of protein loaded onto the disc at the 10% breakthrough was determined through analysis of the chromatogram in the Unicorn software (GE Healthcare).

For anion exchange material the loading material was 1 mg/mL BSA in 10 mMTris to pH 8.

DBCs were determined for the various materials of Preparative Examples 2 and 3. The materials tested are set out as materials 1 to 4 in Table 1 below and the DBCs shown in FIG. 1.

TABLE 1

BSA binding capacities

| | 1 | 2 | 3 | 4 |
|---|---|---|---|---|
| Charge density (µmol/g) | 308 | 775 | 523 | 775 |
| Glycidol (mL) | X | X | 180 | 180 |
| BSA DBC (mg/mL) | 18 | 43 | 62 | 137 |

It can be seen from FIG. 1 that increasing the charge density of the material increases the DBC for BSA. Increasing the amount of polymer covalently bonded to the material also increases the DBC for BSA. The highest capacity for BSA is 7.6× the lowest.

II Separation of Viral Material

Example 1—Separation of Adenovirus Material (AV)

Adenovirus material produced in Preparative Example 4 was subjected to a bind-elute chromatographic separation process using the materials produced in Preparative Examples 2 and 3.

The following chromatographic method was used for the separation.

TABLE 2

Chromatography Method 1

| Step | Volume (mL) |
|---|---|
| 125 µL nanofibre adsorbent volume | |
| 80 mV/min (0.75 second residence time) | |
| Equilibration | 15 |
| Load | 20 |
| Column Wash | 15 |
| 10 mM Tris | |
| Gradient (linear) | 60 |
| 0-40% 10 mM Tris 1M NaCl | |
| Gradient (step) | 2 |
| 100% 10 mM Tris 1M NaCl | |
| Column Wash | 10 |
| 10 mM Tris 1M NaCl | |
| Equilibration | 15 |
| 10 mM Tris | |

Analysis of Chromatograms

Figure 2:
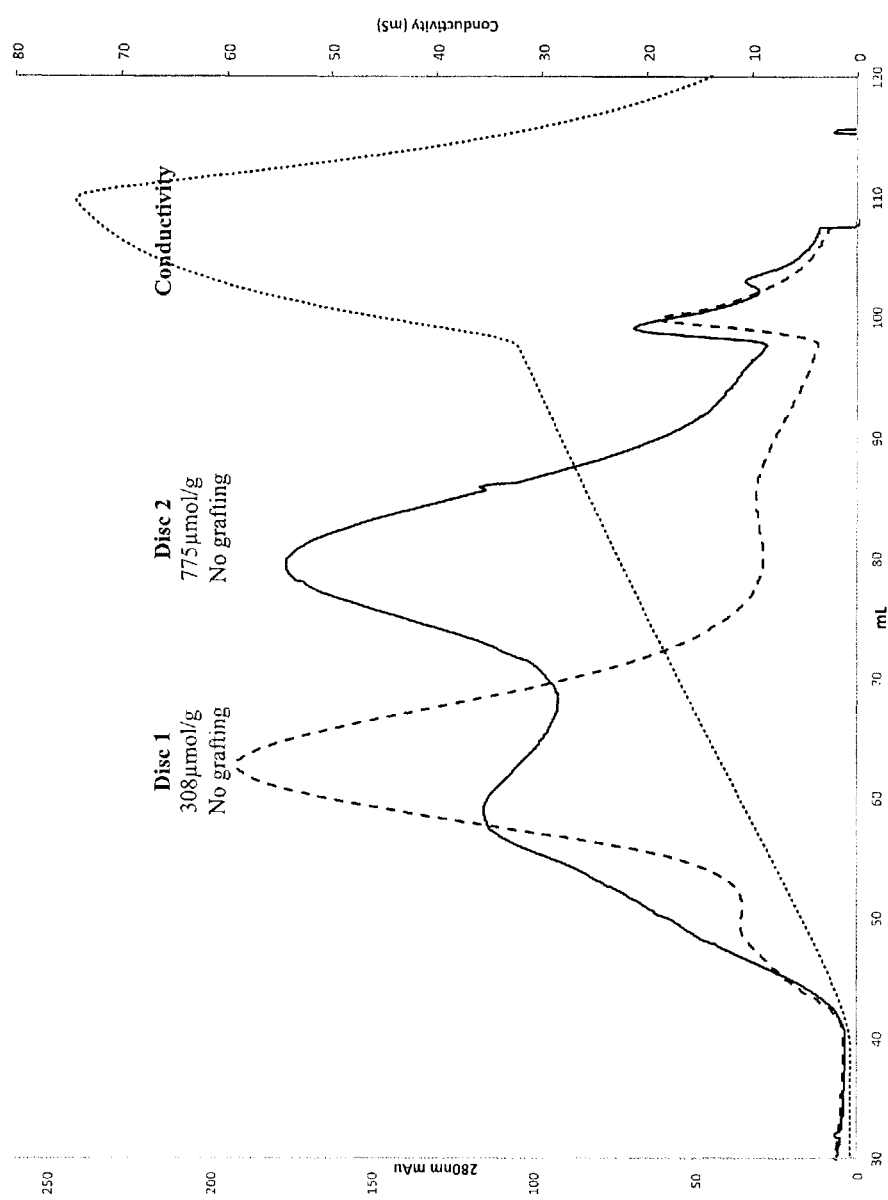
FIG. 2 shows a comparison of low charge density vs high charge density material where the material has not been grafted
Figure 3:
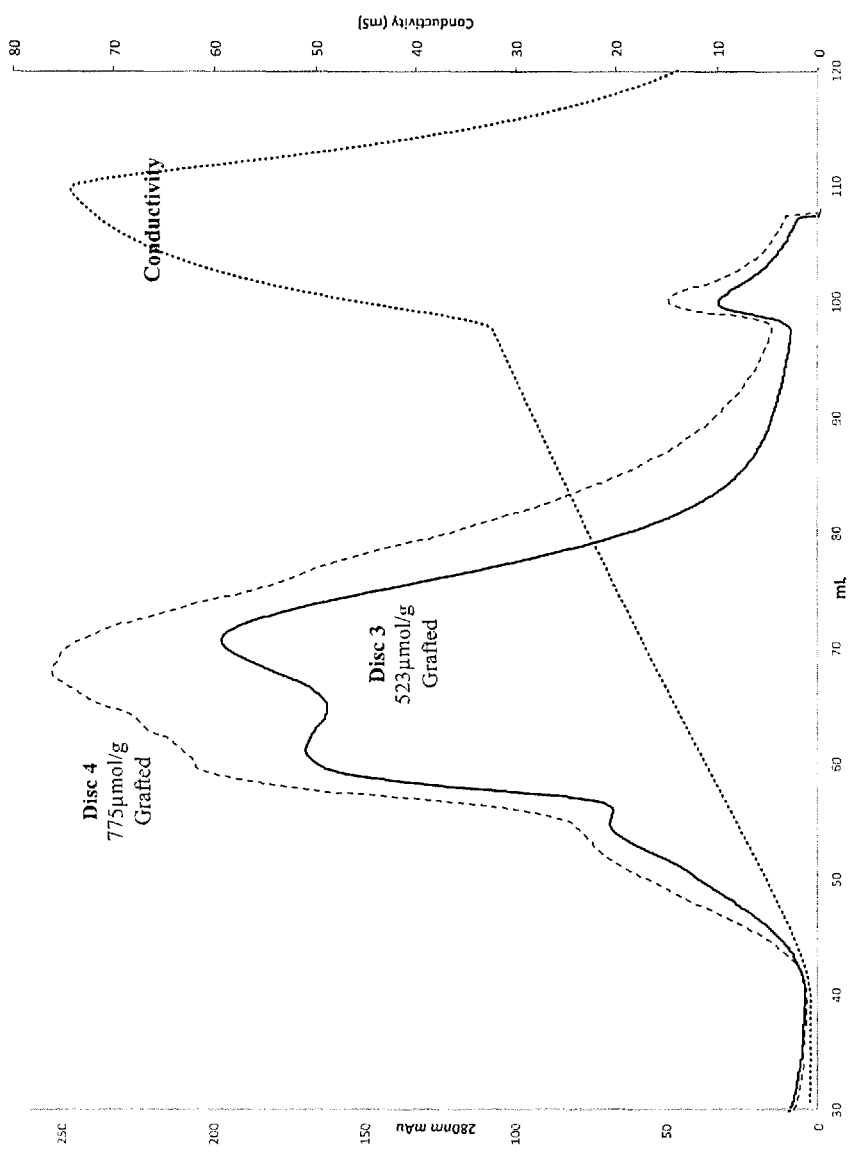
FIG. 3 shows a comparison of low charge density vs high charge density material where the material has been grafted
Figure 4:
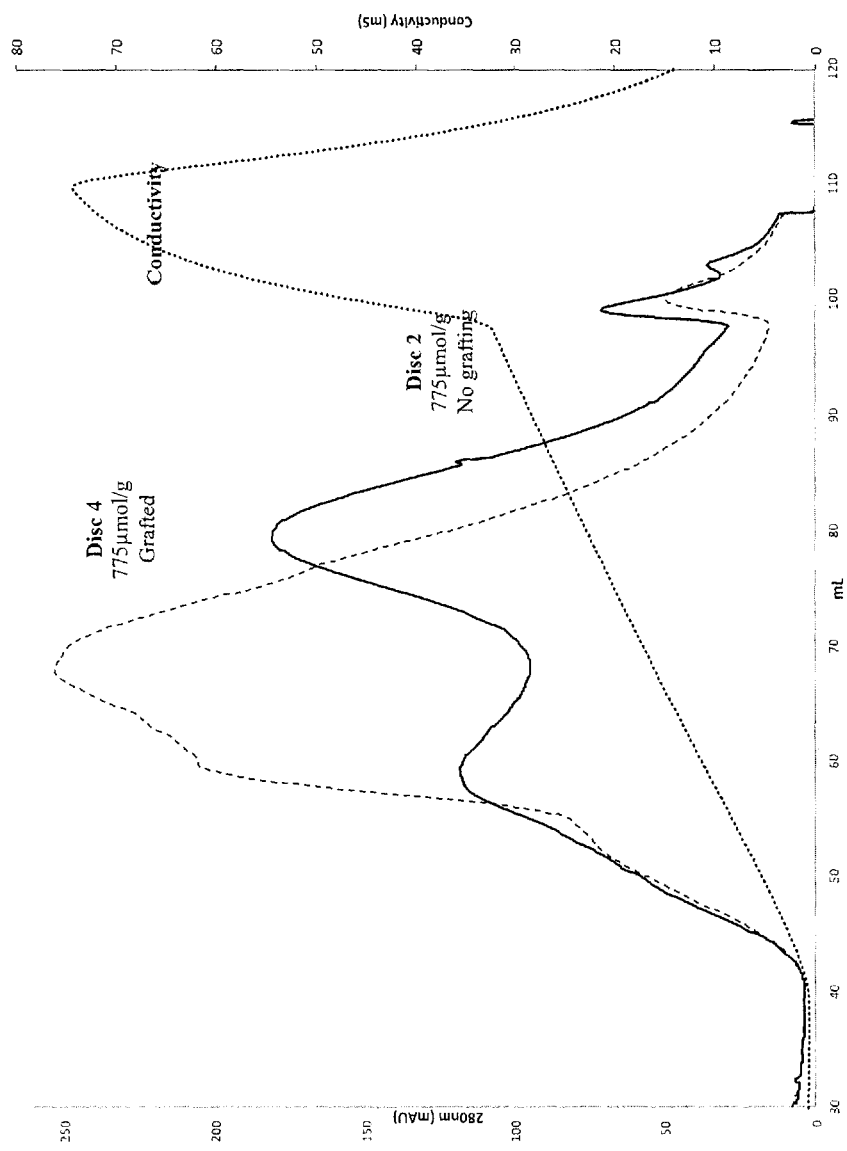
FIG. 4 shows a comparison of grafted and non-grafted materials both with high charge density

The resultant chromatograms for the materials 1 to 4 are compared in FIGS. 2 to 4.

FIG. 2 compares materials 1 and 2. This shows that an increase in charge density of the non-grafted material substantially alters the shape of the chromatogram. There also appears to be a second species present in the chromatogram using material 2.

For material to which polymer chains are covalently bonded (grafted), the opposite relationship is seen. FIG. 3 compares materials 3 and 4. This demonstrates that for grafted materials the apparent resolution of the separation is reduced when the charge density and binding capacity of the adsorbent (for BSA) is increased.

When comparing grafted and non-grafted materials of the same charge density it can be seen that the better resolution is achieved for materials which have not been grafted, and that resolution of species is improved using materials having a higher charge density.

FIG. 4 compares materials 2 and 4.

Adenovirus Capacity Data

Figure 5:
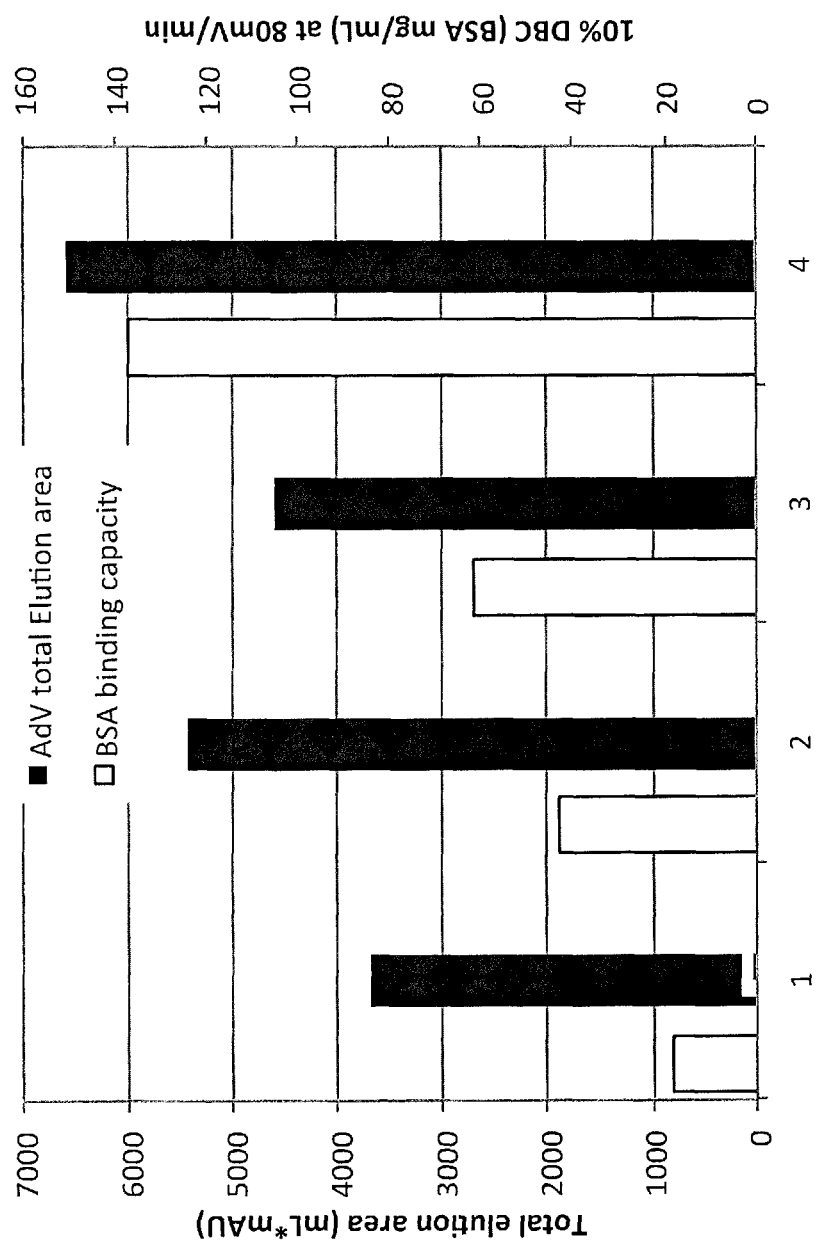
FIG. 5 shows the capacity of materials for AdV vectors and for BSA

The total elution area for the four different chromatography processes (using materials 1 to 4) was compared to determine the capacity of the materials. The results are shown in FIG. 5. From this it can be seen that the highest binding material binds 1.8× more AdV than the lowest binding material.

Unexpectedly, the difference in capacity for the AdV preparation is far less pronounced when compared to the difference in capacity of the same materials for BSA, where the difference between strongest and weakest binding was 7.6×.

This shows that materials optimized for high binding capacities of small molecules such as BSA (66 KDa) may be unsuited to binding and separating large vector materials which are many orders of magnitude larger (20-110 nm).

Example 2—Separation of Adeno-Associated Virus (AAV) Material

Adenovirus material produced in Preparative Example 5 was subjected to a bind-elute chromatographic separation process using a materials produced in accordance with the method of Preparative Example 2 having a charge density of 820 μmol/g. It was prepared using the method of Preparative Example 2 using 120 mL of GMAC.

The following chromatographic method was used for the separation.

TABLE 3

Chromatography Method 2

| Step | Volume (mL) |
| --- | --- |
| Equilibration | |
| Load | |
| Column Wash | 5 |
| Bis Tris Propan 10 mM pH 8 | |
| Gradient (step) | 0 |
| 0-1% Bis Tris Propan 10 mM 1M NaCl | |
| Gradient (gradient) | 25 |
| 1-2% Bis Tris Propan 10 mM 1M NaCl | |
| Gradient (gradient) | 10 |
| 2-5% Bis Tris Propan 10 mM 1M NaCl | |
| Hold | 10 |
| 5% Bis Tris Propan 10 mM 1M NaCl | |
| Wash | 12 |
| 100% Bis Tris Propan 10 mM 1M NaCl | |

Analysis of Chromatograms

Figure 6:
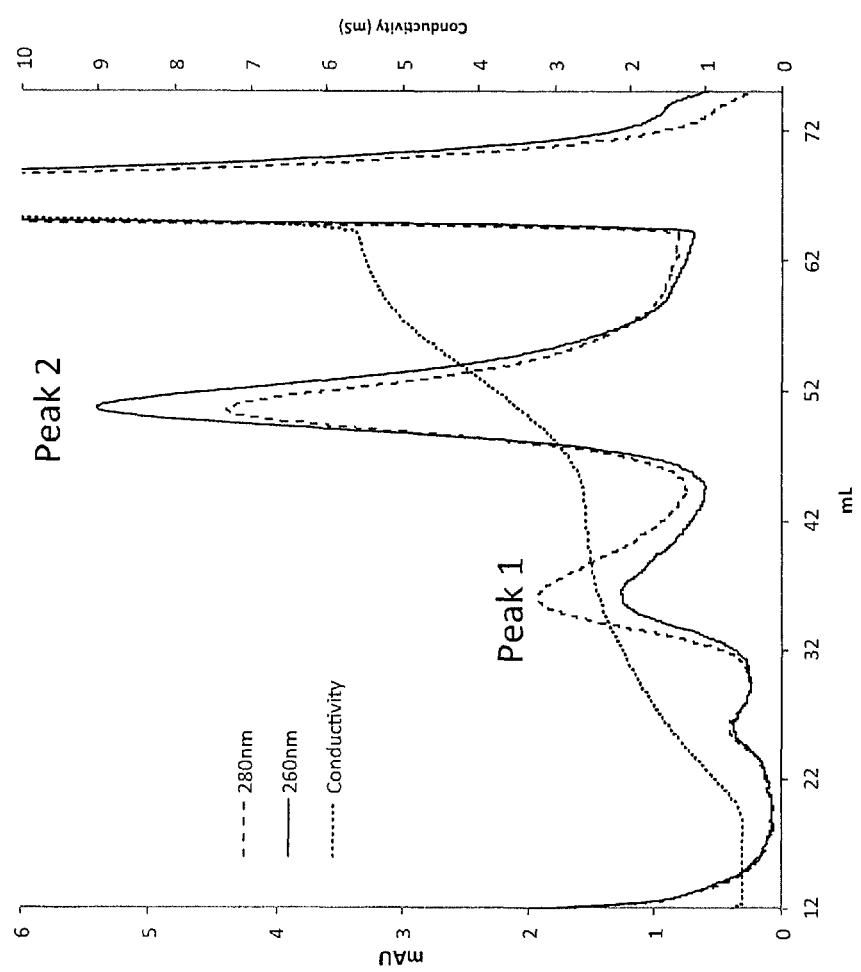
FIG. 6 shows a chromatogram of AAV material

The resultant chromatogram is shown as FIG. 6. This shows two clear peaks, which were thought to be packed and unpacked vector material. This was analysed further using known techniques (Western blotting and PCR)

Western Blotting Analysis

Peaks 1 and 2 from FIG. 6 were analysed for AAV vector capsid proteins via western blotting using known methods (e.g. as discussed in http://www.abcam.com/ps/pdf/protocols/wb-beginner.pdf). The Western blotting trace is shown as FIG. 7. From this it can be seen that the capsid proteins which are present in the load are also present in both Peaks 1 and 2.

PCR Analysis

PCR analysis was carried out on fractions of peaks 1 and 2 from FIG. 6 to amplify the GFP DNA sequence. This was carried out using known methods (Martin Lock et al., 2010).

Figure 8:
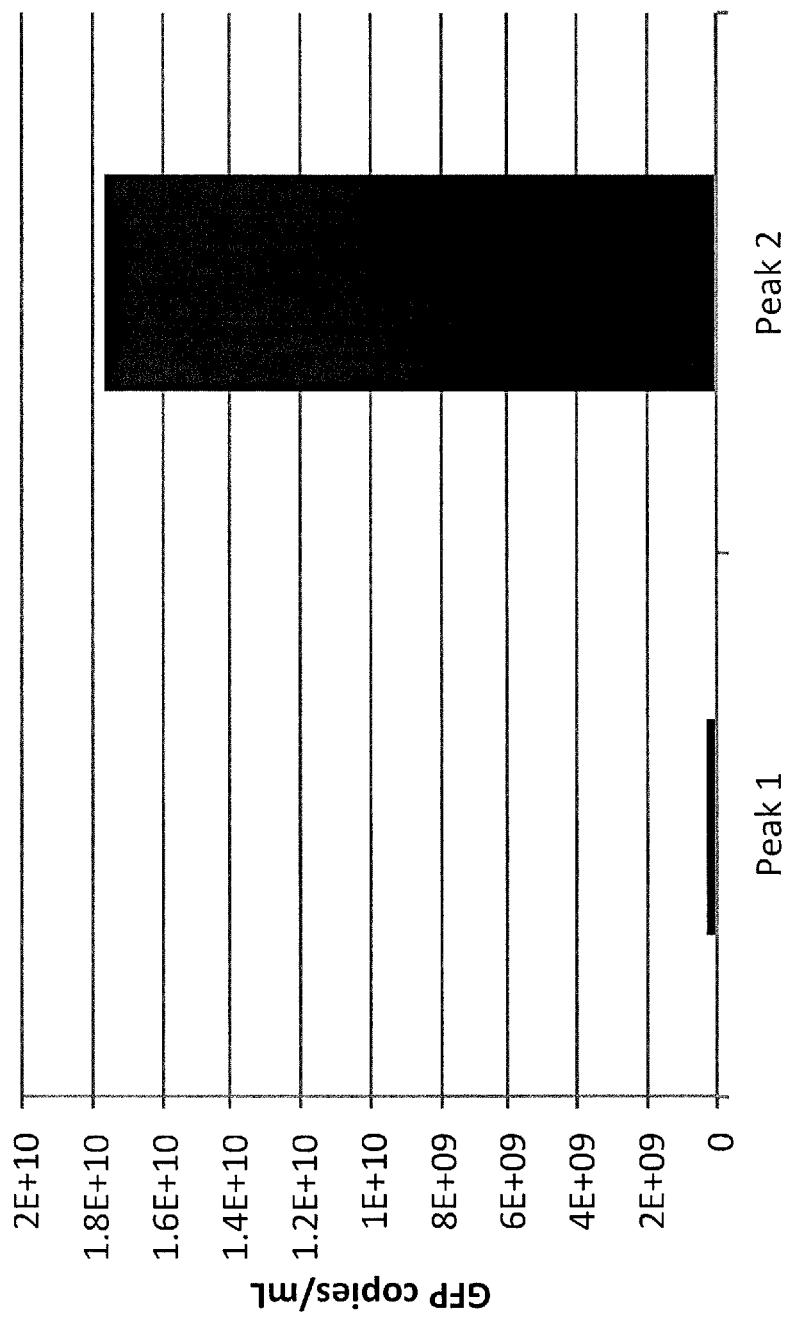
FIG. 8 shows PCR results of fractions collected from the AAV separation

The results of the PCR analysis are shown as FIG. 8. This clearly shows that it is peak 2 that contains the GFP DNA sequence. That makes it clear that it is peak 2 that contains the active packed vector. Peak 1, however, does not contain the GFP DNA sequence.

Figure 7:
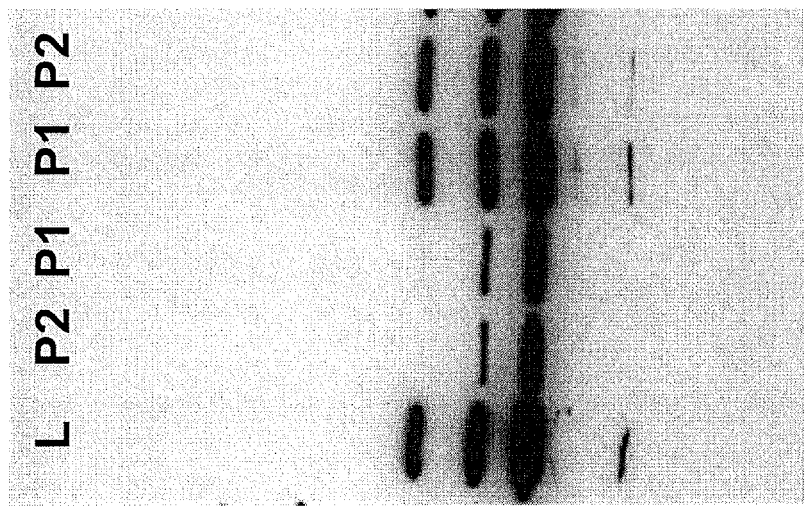
FIG. 7 shows a Western blot of AAV capsid proteins

Taking FIGS. 7 and 8 together it is clear that the chromatographic separation process of the invention has separated a mixture of packed and unpacked vector material into DNA containing packed vector and vectors that do not contain the DNA RECTIFIED SHEET (RULE 91) ISA/EP payload. Referring back to FIG. 6, it is clear that both the packed and unpacked peaks elute at a conductivity at less than 6 mS.

Example 3—Comparison of Process of the Invention with CsCl Gradient Centrifugation Adenovirus material produced in Preparative Example 6 was subjected to a bind-elute chromatographic separation process using the same material and method as Example 2 above.

The Packed peak identified using the characteristic relationship between the 260 nm and 280 nm signal (as seen in FIG. 6) was collected and dialysed into Bis Tris Propan 10 mM pH 8.

A separate sample of the same adenovirus material (produced in Preparative Example 6) was also subjected to CsCl gradient centrifugation separation using a known method (Martin Lock et al., 2010). Both Packed and Unpacked virus material was obtained via this method (dialyzed into Bis Tris Propan 10 mM pH 8) and identified as CsCl-Packed and CsCl unpacked respectively. This material was then compared to material separated using the process of the invention.

The purified Packed material from the chromatographic separation of the invention was analysed using the same material and method as set out in Example 2. Essentially, the same materials and methods are used, but as analytical rather than preparation chromatography. A chromatogram was produced to characterize the material.

The CsCl-Packed material was analysed in the same manner. A chromatogram was produced to characterize the material.

Figure 9:
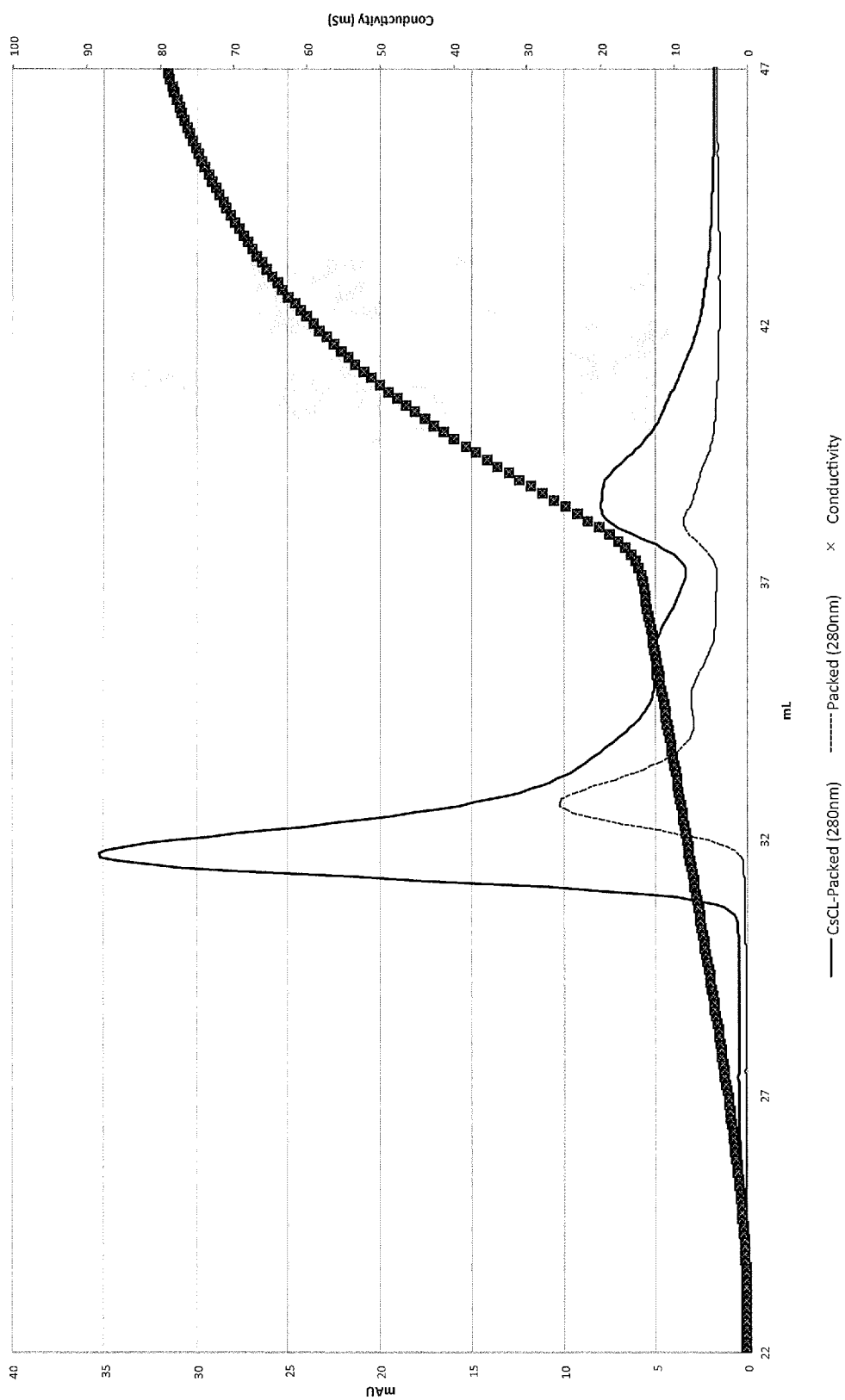
FIG. 9 shows a chromatogram comparing CsCl-Packed material and Packed material obtained from the chromatographic separation of the invention FIG. 10 provides a further comparison of CsCl material and material obtained from the chromatographic separation of the invention

The chromatograms of the Packed material and CsCl-Packed material are shown overlaid as FIG. 9. From this it can be seen there is a high level of similarity between the two traces demonstrating that the products of the two methods are comparable.

For a further comparison of the CsCl method and the process of the present invention, CsCl-Unpacked material was mixed with Packed material and the resultant mixture analysed in the same manner as the Packed material and CsCl-Packed material set out above.

Figure 10:
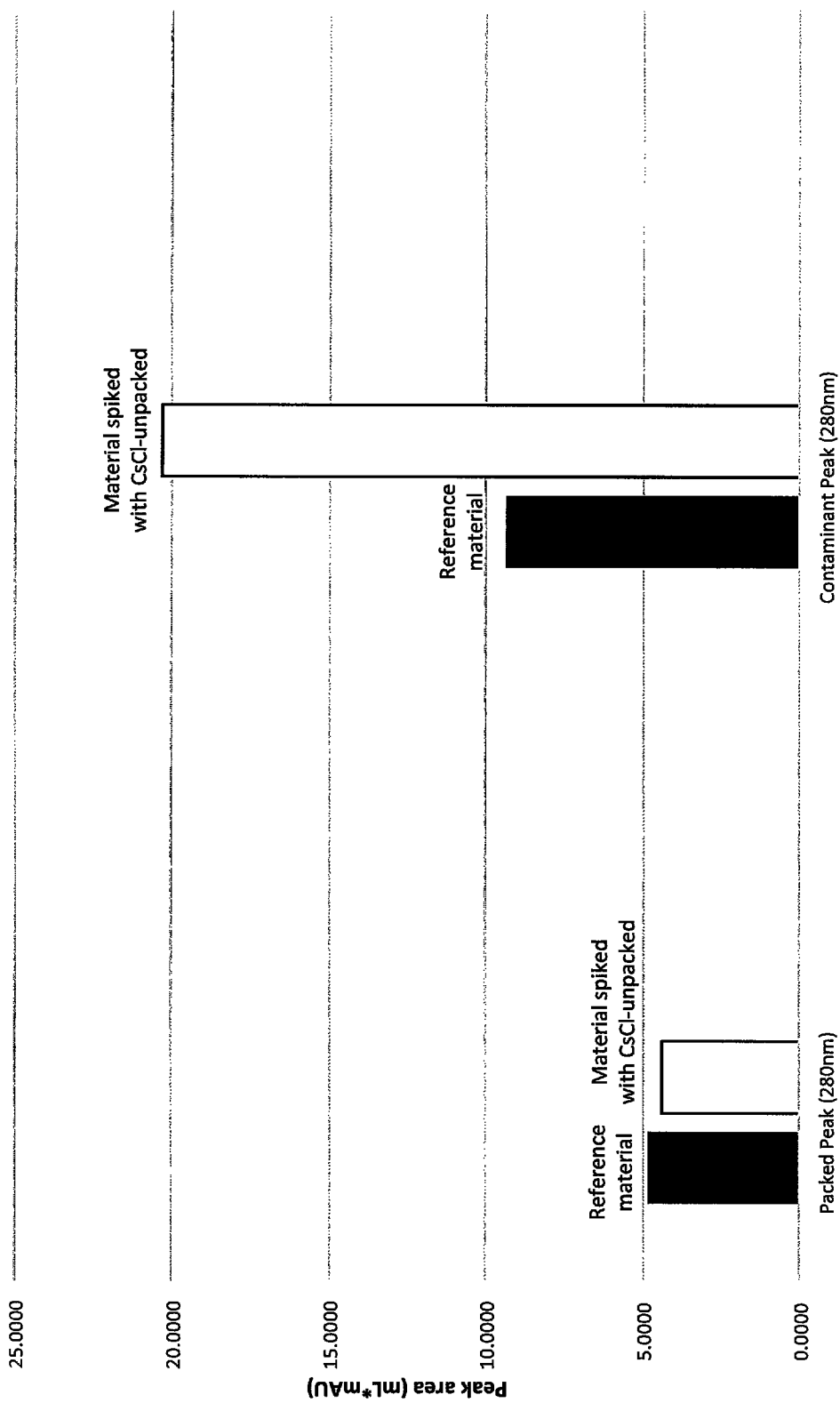

A chromatogram was generated. The relative sizes of the Packed and contaminant peaks are compared in FIG. 10.

From this it can be seen that spiking in the CsCl-Unpacked material does not contribute to the size of the Packed peak. This demonstrates that the Packed peak (and hence Packed fraction obtained using the process of the invention) does not contain un-packed vector. From FIG. 10 it can also be seen that the CsCl-Unpacked material contributes significantly to the contaminant peak. This indicates that the Packed peak (and hence fraction) produced using the invention is of high purity.

REFERENCES

All references cited herein are incorporated herein by reference.

Burova, E., & Ioffe, E. (0000). Chromatographic purification of recombinant adenoviral and adeno-associated viral vectors: methods and implications. *Gene Ther*, 12(S1), S5-S17.

Burova, E., & Ioffe, E. (2005). Chromatographic purification of recombinant adenoviral and adeno-associated viral vectors: methods and implications. *Gene Ther*, 12 *Suppl* 1, S5-17. doi: 10.1038/sj.gt.3302611

Davila, M. L., Riviere, I., Wang, X., Bartido, S., Park, J., Curran, K., . . . Brentjens, R. (2014). Efficacy and Toxicity Management of 19-28z CAR T Cell Therapy in B Cell Acute Lymphoblastic Leukemia. *Science Translational Medicine*, 6(224), 224ra225-224ra225. doi: 10.1126/scitranslmed.3008226

Kaplitt, M. G., Feigin, A., Tang, C., Fitzsimons, H. L., Mattis, P., Lawlor, P. A., . . . During, M. J. Safety and tolerability of gene therapy with an adeno-associated virus (AAV) borne GAD gene for Parkinson's disease: an open label, phase I trial. *The Lancet*, 369(9579), 2097-2105. doi: http://dx.doi.org/10.106/S0140-6736(07)60982-9

Lee, D. S., Kim, B. M., & Seol, D. W. (2009). Improved purification of recombinant adenoviral vector by metal affinity membrane chromatography. *Biochem Biophys Res Commun*, 378(3), 640-644. doi: 10.1016/j.bbrc.2008.11.096

Lock, M., Alvira, M., Vandenberghe, L. H., Samanta, A., Toelen, J., Debyser, Z., & Wilson, J. M. (2010). Rapid, Simple, and Versatile Manufacturing of Recombinant Adeno-Associated Viral Vectors at Scale. *Hum Gene Ther*, 21(10), 1259-1271. doi: 10.1089/hum.2010.055

Lock, M., Alvira, M. R., & Wilson, J. M. (2012). Analysis of particle content of recombinant adeno-associated virus serotype 8 vectors by ion-exchange chromatography. *Hum Gene Ther Methods*, 23(1), 56-64. doi: 10.1089/hgtb.2011.217

Nathwani, A. C., Reiss, U. M., Tuddenham, E. G. D., Rosales, C., Chowdary, P., McIntosh, J., . . . Davidoff, A. M. (2014). Long-Term Safety and Efficacy of Factor IX Gene Therapy in Hemophilia B. *New England Journal of Medicine*, 371(21), 1994-2004. doi: doi: 10.1056/NEJMoa1407309

Qu, G., Bahr-Davidson, J., Prado, J., Tai, A., Cataniag, F., McDonnell, J., . . . Wright, J. F. (2007). Separation of adeno-associated virus type 2 empty particles from genome containing vectors by anion-exchange column chromatography. *J Virol Methods*, 140(1-2), 183-192. doi: 10.1016/j.jviromet.2006.11.019

Urabe, M., Xin, K.-Q., Obara, Y., Nakakura, T., Mizukami, H., Kume, A., . . . Ozawa, K. (2006). Removal of Empty Capsids from Type 1 Adeno-Associated Virus Vector Stocks by Anion-Exchange Chromatography Potentiates Transgene Expression. *Mol Ther*, 13(4), 823-828.

Vellekamp, G., Porter, F. W., Sutjipto, S., Cutler, C., Bondoc, L., Liu, Y.-H., . . . Zhuang, S. (2001). Empty Capsids in Column-Purified Recombinant Adenovirus Preparations. *Hum Gene Ther*, 12(15), 1923-1936. doi: 10.1089/104303401753153974

Wickramasinghe, S. R., Carlson, J. O., Teske, C., Hubbuch, J., & Ulbricht, M. (2006). Characterizing solute binding to macroporous ion exchange membrane adsorbers using confocal laser scanning microscopy. *Journal of Membrane Science*, 281(1-2), 609-618. doi: http://dx.doi.org/10.1016./i.memsci.2006.04.032

Wright, J. F., Le, T., Prado, J., Bahr-Davidson, J., Smith, P. I-H., Zhen, Z., . . . Qu, G. (2005). Identification of factors that contribute to recombinant AAV2 particle aggregation and methods to prevent its occurrence during vector purification and formulation. *Mol Ther*, 12(1), 171-178.

The invention claimed is:

1. A process for recovering a full viral product from a composition comprising said full viral product and an empty viral product, which process comprises:
   a) contacting the composition with a functionalised chromatography medium, wherein the composition has a dissolved salt concentration such that an electrical conductivity is below 10 mS/cm;
   b) washing the functionalised chromatography medium with a liquid phase of low ionic concentration corresponding to the electric conductivity of a); and
   c) selectively eluting the full viral product from and the empty viral product by contacting the functionalised chromatography medium with a liquid phase of increasing ionic strength;
   wherein the full viral product is an Adenovirus or an Adeno-associated virus or corresponding viral particle containing one or more polynucleotides, and wherein the empty viral product is an Adenovirus or an Adeno-associated virus or corresponding viral particle substantially devoid of polynucleotides; and
   wherein the functionalised chromatography medium comprises one or more non-woven non-grafted cellulose nanofibers having a density of 600 μmol to 1000 μmol trimethylammonium ligand groups per gram of functionalised chromatography medium.

2. The process according to claim 1, wherein the full viral product comprises a plurality of viruses, virus particles, viral cores, membrane-stripped viruses, viral cores with outer membrane(s) removed and/or capsids removed, or proviruses, each of which is capable of infecting a cell.

3. The process according to claim 1, wherein the full viral product comprises a plurality of viral vectors each containing one or more transgenic polynucleotides.

4. The process according to claim 1, wherein the empty viral product comprises a plurality of viruses, virus particles/virions, virus-like particles, viral cores, membrane-stripped viruses, viral cores with outer membrane(s) removed and/or capsids removed or proviruses, each of which is incapable of infecting a cell.

5. The process according to claim 1, wherein the empty viral product comprises a plurality of viruses, virus particles/virions, virus-like particles viral cores, membrane-stripped viruses, viral cores with outer membrane(s) removed and/or capsids removed or proviruses, each of which lacks a complete viral genome.

6. The process according to claim 1, wherein the functionalised chromatography medium is suitable for use in a chromatography method chosen from the group consisting of ion exchange, hydrophobic interaction and mixed mode methods.

7. The process according to claim 1, wherein the functionalised chromatography medium has a dynamic binding capacity of up to 50 mg/mL (10% breakthrough).

8. The process according to claim 1, wherein the functionalised chromatography medium is in the form of a membrane or sheet.

9. The process according to claim 1, wherein the functionalised chromatography medium is in the form of a membrane or sheet and the composition is passed through a holder comprising one or more said membranes or sheets and optionally one or more frits or other spacer materials.

10. The process according to claim 9, wherein the composition is passed through the holder such that the path length through said one or more membranes or sheets is less than 2 mm, or the total path length through membranes, sheets, frits and other spacer materials is less than 50 mm.

11. The process according to claim 1, wherein the composition is contacted with the functionalised chromatography medium for a period of time of one minute or less.

12. The process according to claim 1, wherein the one or more polynucleotides are one or more nucleic acids chosen from DNA and RNA, including siRNA.

13. The process according to claim 1, wherein the empty viral product is collected as a secondary product.

* * * * *